(12) United States Patent
Merz, Jr. et al.

(10) Patent No.: US 7,904,283 B2
(45) Date of Patent: Mar. 8, 2011

(54) QUANTUM MECHANICS BASED METHOD FOR SCORING PROTEIN-LIGAND INTERACTIONS

(75) Inventors: Kenneth M. Merz, Jr., Port Matilda, PA (US); Kaushik Raha, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 771 days.

(21) Appl. No.: 10/844,258

(22) Filed: May 12, 2004

(65) Prior Publication Data

US 2005/0027458 A1   Feb. 3, 2005

Related U.S. Application Data

(60) Provisional application No. 60/469,939, filed on May 13, 2003.

(51) Int. Cl.
  *G06G 7/48* (2006.01)
  *G01N 33/48* (2006.01)
  *G06G 7/58* (2006.01)
(52) U.S. Cl. ................................ 703/11; 702/19; 703/12
(58) Field of Classification Search .................. None
  See application file for complete search history.

(56) References Cited

U.S. PATENT DOCUMENTS

| | | | |
|---|---|---|---|
| 5,612,894 A | 3/1997 | Wertz |
| 5,726,014 A | 3/1998 | Edwards et al. |
| 5,995,908 A | 11/1999 | Pullen |
| 6,178,334 B1 | 1/2001 | Kolossvary |
| 6,185,548 B1 | 2/2001 | Schwartz et al. |

OTHER PUBLICATIONS

Beck et al. "Some Biological Applications of Semiempirical MO Theory" Perspectives in Drug Discovery and Design (1998) pp. 131-159.*

Massova et al. "Combined molecular mechanical and continuum solvent approach to (MM-PBSA/GBSA) to predict ligand binding" Perspectives in Drug discovery and Design (2000) vol. 18, pp. 113-135.*

Pang et al. "EUDOC: A Computer Program for Identification of Drug Interaction Sites in Macromolecules and Drug Leads from Chemical Databases" Journal of Computational Chemistry (2001) vol. 22, pp. 750-1771.*

Vincent et al. "Parallel implementation of a divide and conquer semiemperical algorithm" Theoretical Chemistry Accounts (1998) vol. 99, pp. 220-223.*

Gao, J. The hydration and solvent polarization effects of nucleotide bases. Biophysical Chemistry. 1994, vol. 51, pp. 253-261.

Khandogin et al. Quantum Mechanical Characterization of Nucleic Acids in Solution: A Linear-Scaling Study of Charge Fluctuations in DNA and RNA. J. Phys. Chem. 2002, vol. 106, pp. 7693-7703.

Zheing et al. Statistical Survey of Transition States and Conformational Substrates of the Sperm Whale Myoglobin—CO Reaction System. J. Chem. Soc. 1996, vol. 118, pp. 2818-2824.

* cited by examiner

*Primary Examiner* — Eric S. DeJong
(74) *Attorney, Agent, or Firm* — Barbara E. Johnson, Esq.

(57) ABSTRACT

The present invention provides for the first time a quantum mechanics-based method for scoring protein-ligand interactions and binding affinity predictions, using quantum mechanical Hamiltonians and/or a combined quantum mechanical/molecular mechanical approach, and Poisson-Boltzmann (PB)-based solvation methods. Also provided is a method for using quantum mechanics to describe the enthalpic and solvation effects of binding. The method comprises comparing the calculated binding affinities to experimental values in order to measure the success of the method. The methods disclosed herein may further be used to score protein and drug or protein and inhibitor interactions. The present method can predict the free energy of binding of protein-ligand complexes with high accuracy so as to enable lead optimization, thus serving as a powerful tool in computational drug design.

8 Claims, 10 Drawing Sheets

Table I.

| | ΔHF | ΔLJ6 | ΔGsolv | ΔHF+ΔLJ6+ΔGolv |
|---|---:|---:|---:|---:|
| [a]SH3-3BP2 | 254.165 | -182.148 | 227.431 | 299.448 |
| SH3-3BP2 * | -167.213 | -83.3437 | 232.911 | -17.6457 |
| [a]IG-ACEQFHP | 1178.57 | -130.038 | -356.53 | 692.002 |
| IG-ACEQFHP * | 65.0757 | -113.858 | 13.5306 | -35.2517 |
| [a]IG-ACEQFHPNHE | 733.996 | -110.903 | 219.204 | 842.297 |
| IG-ACEQFHPNHE * | 8.49735 | -88.16 | 39.3577 | -40.30495 |
| [a]Endothiapepsin-PD125754 | -907.068 | -118.345 | 227.18 | -798.233 |
| Endothiapepsin-PD125754 * | 247.103 | -122.422 | -107.408 | 17.273 |
| [a]SH2-cmFEEI | -159.635 | -100.719 | 401.558 | 141.204 |
| SH2-cmFEEIm * | -364.496 | -100.358 | 404.773 | -60.081 |
| [b]HIVP-A77003 | -13.0154 | -163.1 | 129.582 | -46.5334 |
| HIVP-A77003 * | -75.6484 | -155.962 | 139.247 | -92.3634 |
| [b]HIVP-A78791 | -34.2124 | -161.08 | 127.488 | -67.8044 |
| HIVP-A78791 * | -46.4136 | -150.164 | 137.158 | -59.4196 |
| [b]TIM-Phosphoglycerate | -440.837 | -66.5114 | 578.333 | 70.9846 |
| TIM-Phosphoglycerate * | -465.392 | -63.0707 | 585.342 | 56.8793 |

Table II.

| Enzyme/Protein | Inhibitor/Ligand | Crystallographic Conditions | | | Binding Assay Conditions[a] | | | Activity | |
|---|---|---|---|---|---|---|---|---|---|
| | | pH | Buffer | Ki | pH | Buffer | Ki | EC50[b] | IC50[c] |
| HIV-1 Protease | A77003 | 6.2 | 0.125 M MES | 12 (pM) | 4.6 | 0.125 M Sodium Acetate | 84 (pM) | 0.2 (µM) | |
| HIV-1 Protease | A76889 | 6.2 | 0.125 M MES | 112 (pM) | 4.6 | 0.125 M Sodium Acetate | 1000 (pM) | 1.54 (µM) | |
| HIV-1 Protease | A76928 | 6.2 | 0.125 M MES | 77 (pM) | 4.6 | 0.125 M Sodium Acetate | 11 (pM) | 0.17 (µM) | |
| HIV-1 Protease | A78791 | 6.2 | 0.125 M MES | 35 (pM) | 4.6 | 0.125 M Sodium Acetate | 4 (pM) | 0.16 (µM) | |
| Endothiapepsin | PD125967 | 4.6 | 0.1 M Sodium Acetate | | 3.5 | 0.1 M Sodium Formate | 242 (nM) | | 170 (nM) |
| Endothiapepsin | PD125754 | 4.6 | 0.1 M Sodium Acetate | | 3.5 | 0.1 M Sodium Formate | 16180 (nM) | | 22 (nM) | a Fluorometric binding assay using a fluorogenic substrate. b IC50 is the concentration of a drug that is required for 50% inhibition of viral replication in vivo. c EC50 is the plasma concentration required for obtaining 50% of the maximum effect in vivo in a cytopathic effect assay.

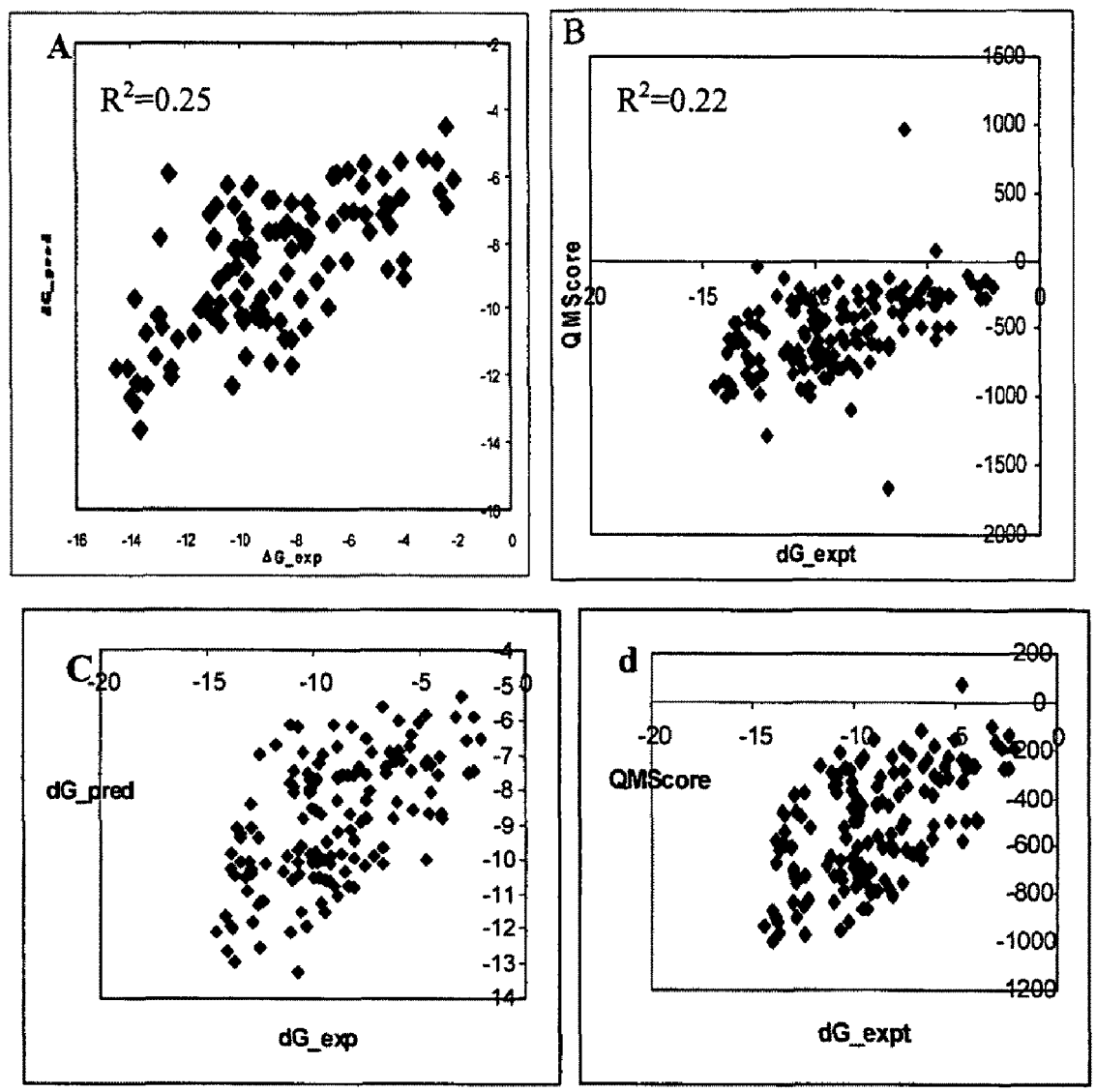
Figs. 3A-D.

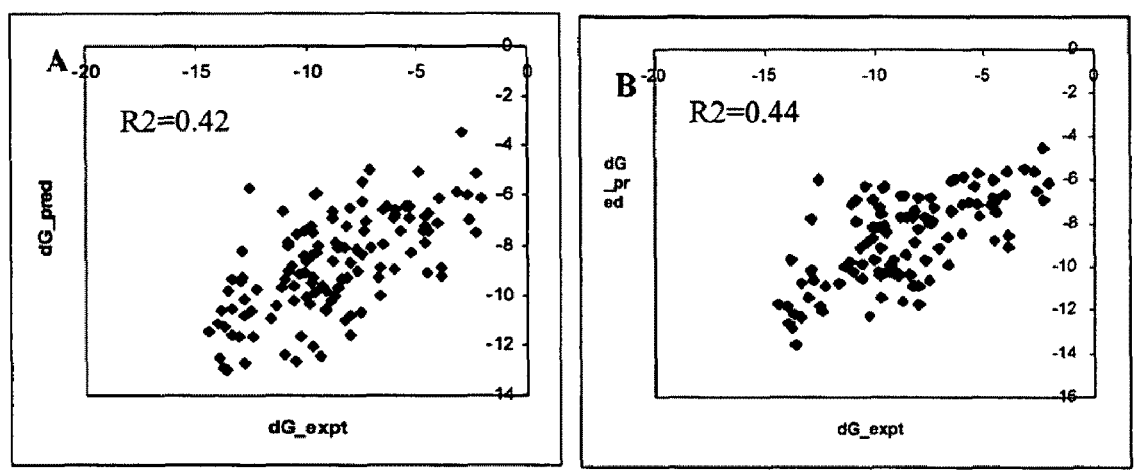
Figs. 4A-B.

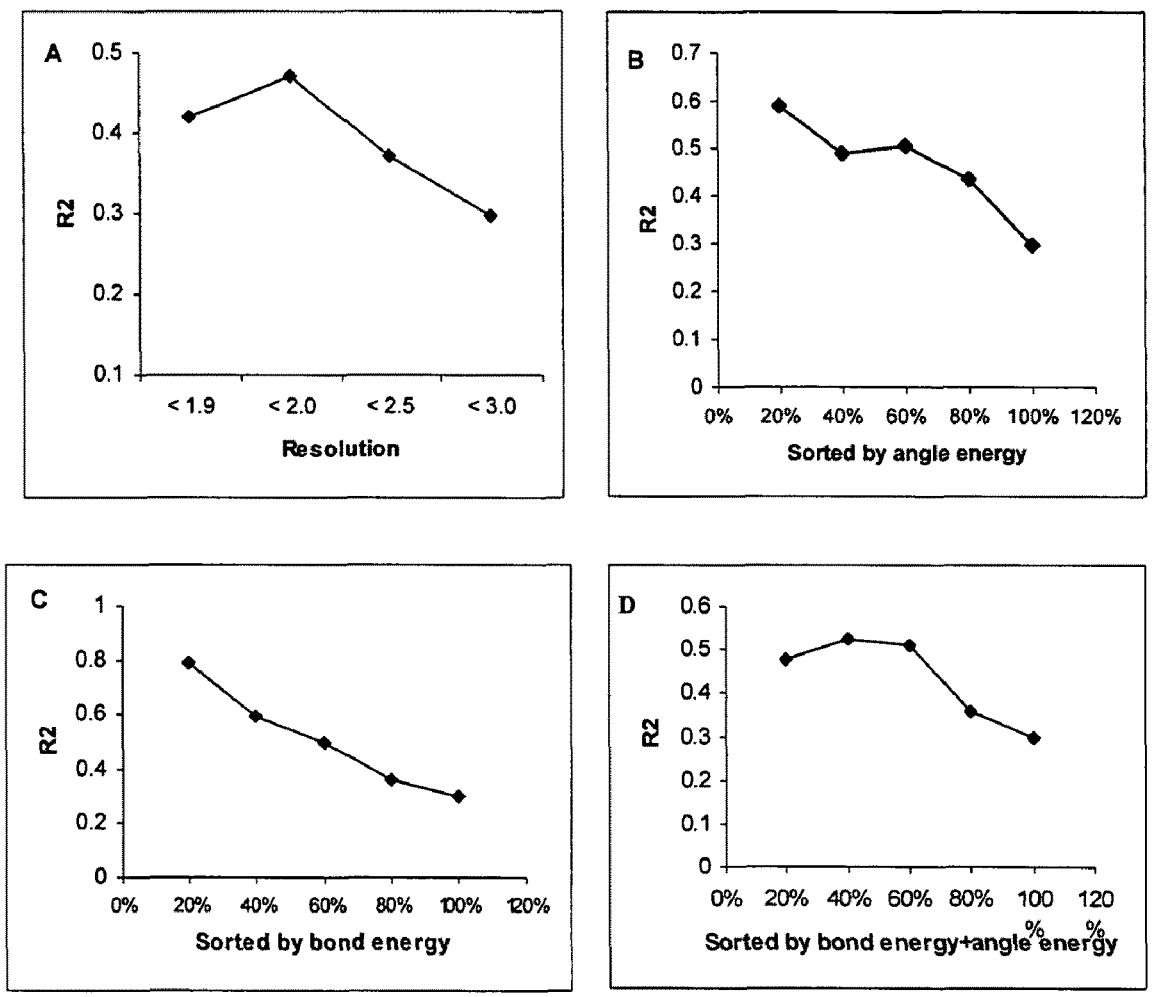
Figs. 5A-D.

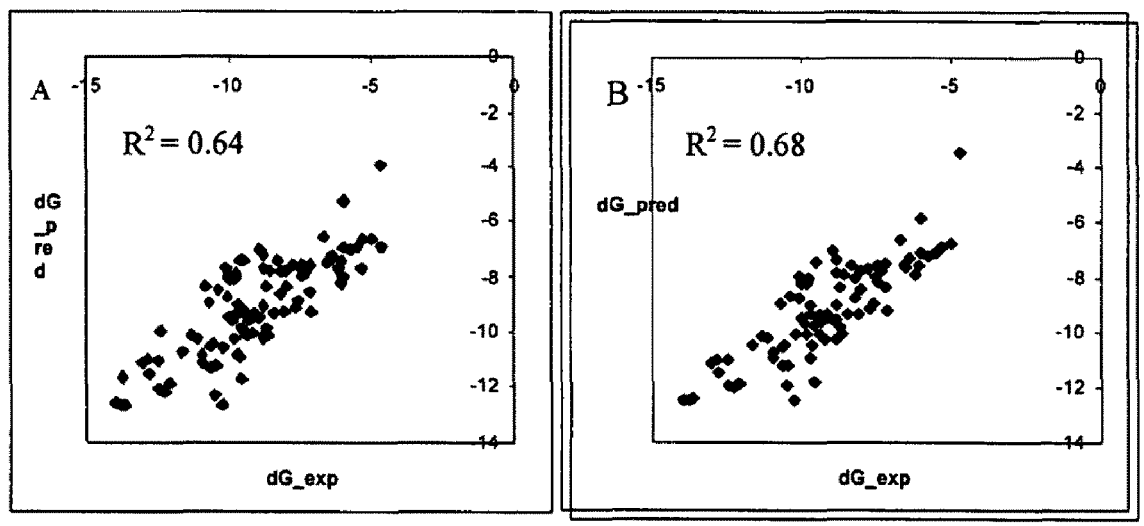
Figs. 6A-B.

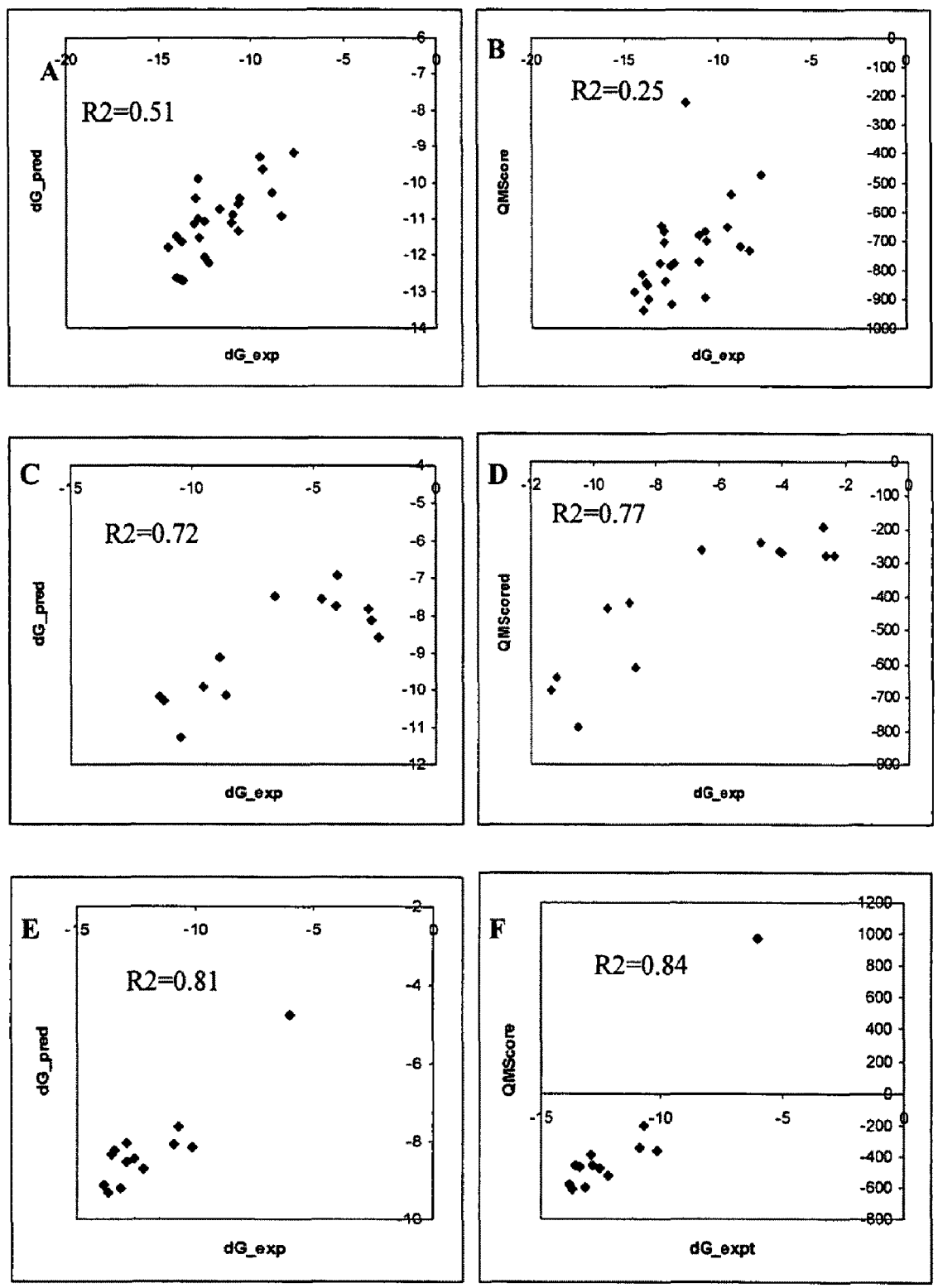
Fig. 7A-F.

QUANTUM MECHANICS BASED METHOD FOR SCORING PROTEIN-LIGAND INTERACTIONS

The present application claims priority to U.S. Provisional Application No. 60/469,939, filed May 13, 2003, which is incorporated herein by reference.

STATEMENT REGARDING FEDERALLY SPONSORED RESEARCH

This invention was made with government support under Grant No. MCB-0211639, awarded by the National Science Foundation. The Government has certain rights in the invention.

BACKGROUND OF THE INVENTION

1. Field of the Invention

The present invention relates to protein-ligand interactions. More particularly, the present invention provides a quantum mechanics-based method for scoring protein-ligand interactions and binding affinity predictions for computational drug design.

2. Description of Related Art

The study of protein-ligand interactions has been an area of active research with widespread implications, especially its potential impact on rational drug discovery and design. In particular, the prediction of free energy of binding ($\Delta G_{bind}$), referred to as "scoring," via computational methods based on a description of the energetic components of binding, has proven to be a major challenge. In spite of all the recent developments in this area, a physically based model that is robust enough to satisfactorily evaluate the binding of ligands to proteins has been elusive.

The lifecycle for the discovery of a new drug typically spans ten to fifteen years. Worldwide research and development (R&D) expenditures by the pharmaceutical industry have been increasing steadily during the past thirty years. The annual R&D outlays for United States pharmaceutical companies reached twenty-six billion dollars in the year 2000. Of the estimated $802 million it now costs to discover a drug and bring it to market, approximately 75% of the overall R&D cost is attributed to failures. Thus, the ability to employ a scoring function that avoids the synthesis of false positives or eliminates the synthesis of false negatives could have a major impact on accelerating the discovery of low moleculer weight ligands that potently and specifically bind to a target. Additionally, the ability to rank analog series could facilitate the identification of alternative compounds in the presence of constraints imposed by pharmacokinetics and toxicity, thus reducing the likelihood of costly late stage failures.

An ideal drug is an exquisite balance of potency, selectivity, pharmacokinetics and toxicity. More importantly, the efficient identification of potent low molecular weight inhibitors would dramatically reduce the number of years it takes to bring important new therapeutics to market for the benefit of patients.

Thus, because of the relentless pressure on the pharmaceutical industry to reduce drug discovery costs, the development of in silico structure-based screening has become a very attractive and cost-effective alternative to traditional medicinal chemistry approaches. Additionally, the development of faster computer hardware, coupled with the development of ever more efficient computational algorithms, has facilitated greatly the screening of a large number and broad range of virtual compounds.

In particular, in silico structure-based screening methods can "dock" a low molecular weight into a biological receptor. Docking methods can be placed into two categories: stochastic methods such as AUTODOCK (Goodsell, D. S. et al., Proteins, 8:195-202, 1990), GOLD (Jones, G. et al., J. Mol. Biol. 267:727-748, 1997), and SAS; or combinatorial methods such as DOCK (Meng, E. C. et al., J. Comput. Chem., 13:380-397, 1992), FlexX (Kramer, B. et al., Proteins: Struct., Funct., Genet., 37:228-241, 1999), Hammerhead and LibDock. Docking is based on the principles of molecular recognition, and the above programs are capable of sampling the conformational space of a low molecular weight molecule and "pose" them in the active site of a protein.

Docking and scoring are interrelated in computational drug design and the success of one depends on the other. Simplistic docking potentials have been reasonably successful in lead identification, library enrichment and virtual high throughput screening (vHTS). Docking of compounds into a receptor binding site and then scoring the docked "pose" is a commonly used methodology for identifying lead compounds. A critical part of drug discovery is in lead optimization, and it is here that the accuracy of scoring functions is more important than the speed of the scoring. Docking algorithms have been reasonably successful in predicting binding modes. However, scoring of the poses in order to predict the binding free energy has proven much more challenging. This is because the pose that is closest to the experimental state is often not ranked energetically as the most favorable pose within a set of decoys. It is believed that docking algorithms reasonably can predict conformational sampling, however, docking functions are not reliable enough to separate native-like answers from alternative solutions.

Current generation scoring functions (SFs) can be grouped into three categories: empirical scoring functions (ESFs), knowledge-based potentials (KBPs) and force-field (FF) methods. ESFs, e.g., LUDU, piecewise linear potential (PLP), VALIDATE and ProteusScore, use empirically derived energetic contributions related to enthalpy ($\Delta H$) and entropy ($\Delta S$) and regression methods to fit it to a set of experimental observations. Cross-validation is done on test sets to test the accuracy of prediction using these functions. The problem with empirical methods is that they can only be as discriminating as the contributions in the scoring function. Usually, the contributions are calculated using simplistic functions, for example, a clash potential for no overlap and a simple geometric function for hydrogen bond interaction. Also, the diversity of a training set is an important factor in the development of such scoring functions (Bohm, H. J. Mol. Des., 12:309-323, 1998).

Knowledge-based methods or potentials (KBPs), such as PMF, SMoG, BLEEP, and DrugScore, are based on statistical mechanics and are borrowed from protein folding studies. The free energy of binding ($\Delta G_{bind}$) is represented as a potential of mean force calculated from frequencies of interatomic contacts from a database of structures (Muegge, I. et al., J. Med. Chem., 42:791-804, 1999). KBPs have been shown to be successful in calculating $\Delta G_{bind}$, however their accuracy depends on the proper definition of the reference state and on the number of structures available to build the potential (Ishchenko, A. V. et al., J. Med. Chem., 43:2770-2780, 2002). Additionally, it is believed that a detailed consideration of steric interactions with a careful treatment of dispersive forces is needed even while using statistical potentials derived from a structural database.

Force-field (FF) or molecular mechanics-based scoring functions use all atom force-field potentials such as AMBER, CHARMM, OPLS, and MMFF to score poses, and have been used frequently in free-energy perturbation (FEP) methods and are implemented by computer programs to evaluate relative $\Delta G_{bind}$ (Kollman, P. A. Chem. Rev., 7:2395-2417, 1993). FEP methods employ molecular dynamics simulations, are computationally expensive and can handle congeneric ligands that differ only in one or two functional groups. Although FEP functions are physically based, there is a problem of transferability of force-field parameters to protein-ligand interactions. FF models have been shown to be extremely powerful in modeling biological systems but generally use simple electrostatic models (Coulomb potentials), which limit their ability to accurately model electrostatic energies. Furthermore, in certain cases, use of a Lennard-Jones 6-12 potential to evaluate non-bonded interactions in ligands that bind very tightly to substrates may lead to artefactual interaction energies. In such cases, a softer potential is better suited for the calculation of non-bonded interactions.

Thus, while the pose generation problem has been solved for the most part, scoring, i.e., $\Delta G_{bind}$, of the poses has been a major challenge.

Quantum mechanics (QM), although not new to the field of molecular interaction, has until recently only been used to study smaller biochemical systems because of the exorbitant computational costs associated with such QM analysis. This is because the numerical effort of conventional electronic structure methods scales as $N^3$ or higher, where N is the number of electrons. For example, both Kohn-Sham density functional theory (DFT) (Kohn, W. et al., Phys. Rev., 140: A1133, 1965) and semiempirical molecular orbital (MO) theory (Dewar, M. J. S., *The Molecular Orbital Theory of Organic Chemistry*, McGraw-Hill, New York, 1969) scale as $N^3$; Hartree-Fock (H-F) Hehre, W. J. et al., *Ab Initio Molecular Orbital Theory*, Wiley, N.Y., 1986) calculations scale according to $N^4$; and post-Hartree-Fock treatments, such as configuration interaction (Hehre, W. J. et al., *Ab Initio Molecular Orbital Theory*, Wiley, N.Y., 1986) and Moller-Plesset theory (Moller, C. et al., Phys. Rev., 46:618, 1934) can exhibit $N^5$ scaling and higher. This nonlinear behavior ultimately places severe limitations on the maximum number of atoms that may be considered in any one system.

Thus, much effort has been made in the development of linear scaling quantum calculations, i.e., methods that require computational effort proportional to the size of the system. Yang (Phys. Rev. Lett., 66:438, 1991) first proposed a divide-and-conquer (D&C) approach and demonstrated that it is possible to attain a solution of linear scaling by localizing the electronic degrees of freedom; Galli et al. (Phys. Rev. Lett., 69:3547, 1992) suggested a linear scaling algorithm and applied tight-binding Hamiltonians; Li et al. (Phys. Rev. B, 47:10891, 1993) introduced a variational method for obtaining the density matrix with cutoff in real space and showed linear scaling in computational effort; and Lee et al. implemented a density matrix D&C approach into linear-scaling semiempirical quantum calculations for large molecules over 9000 atoms on a typical workstation (J. Chem. Phys., 105(7): 2744-2750, 1996).

The use of quantum mechanics avoids the need for force-field-based methods, especially when evaluating electrostatic interactions, where monopole-monopole interactions only can be loosely approximated. Moreover, force-field-based methods inherently are incapable of treating quantum mechanical effects, such as polarization and charge transfer.

Until now, however, there has not been a physically sound, accurate and efficient tool for predicting the free energy of binding, i.e., scoring, of protein-ligand interactions, a tool which would have widespread application in the field of computational drug design.

SUMMARY OF THE INVENTION

The present invention provides for the first time a quantum mechanics (QM)-based method for scoring complete protein-ligand interactions employing superior levels of quantum mechanical theory for predicting the free energy of binding for protein-ligand complexes. In particular, the present invention provides a linear scaling quantum mechanical [O/(N)] methodology that uses a divide and conquer (D&C) approach and quantum mechanical Hamiltonians and/or quantum mechanical/molecular mechanical (QM/MM) Hamiltonians to predict the free energy of binding of protein-ligand complexes. Quantum mechanical approaches that can be used in the present invention include, without limitation, semiempirical Hamiltonians, Hartree-Fock (HF) (ab initio) Hamiltonians, density functional theory (DFT) and quantum Monte Carlo (QMC) Hamiltonians.

The present invention also provides for the first time the use of quantum mechanics to describe the enthalpic and solvation effects of protein-ligand binding. The method involves comparing the calculated binding affinities to experimental values in order to measure the success of the method. Furthermore, the methods disclosed herein may be used to score protein and drug or inhibitor interactions. The present method allows for the prediction of the free energy of binding ($\Delta G_{bind}$) within about 2 to 2.5 kcals/mol, and may be further refined to enable lead optimization, thus serving as a powerful tool in computational drug design.

The method of the present invention uses a Protein Data Bank (PDB) database, in which protein-ligand complexes and at least one experimental binding affinity descriptor, such as calorimetric binding free energies, inhibition constants (Ki's), dissociation constants (Kd's), or IC50s, have been compiled. One objective of the present invention is to obtain the best predictive model from datasets that have considerable noise. In order to provide consistency, all binding affinity descriptors are converted to one free energy of binding descriptor. The protein-ligand complex is preprocessed according to a standard protocol known in the art. The interaction energy is calculated using a thermodynamic cycle, in which the free energy of binding is decomposed into a gas-phase interaction energy and a solvation free energy. The gas phase interaction energy as used herein is the sum of the enthalpic and entropic energy contributions, and the enthalpic energy contribution is calculated as the sum of electrostatic energy and nonpolar interaction energy.

The entropic energy contribution to binding is described by a conformational component and a solvent component. The solvent entropy is the entropy gained by water molecules on being displaced from the active site by the ligand during binding. Solvent entropy is estimated based on polar and apolar surface-area changes during binding. One way to calculate conformational entropy is to evaluate the number of degrees of freedom that are lost in the active site during binding. This is accomplished by counting the number of rotatable bonds in the ligand as a descriptor and the number of rotatable bonds present in the protein sidechains in the active site. Another approach is to estimate the difference in the vibrational entropy of a ligand before and after binding to its protein substrate using a normal mode analysis of the ligand in the protein and in the solvent.

The quantum mechanical portion of the interaction energy is calculated using a semiempirical computer program, referred to as DIVCON, at the AM1 level of theory. DIVCON implements a variation of the density matrix divide and conquer (D&C) method of Yang et al. (J. Chem. Phys. 103:5674-

5678, 1995), i.e., a linear scaling algorithm for solving the Schrodinger equation for large molecules.

The solvation free energy is calculated using a quantum mechanical self-consistent reaction field method (SCRF) implemented in the computer program DIVCON. The solvation free energy of a macromolecule is the sum of the reaction field (electrostatic $G_{RF}$), solute wave function distortion (Gwfd) and nonpolar (Gnp) terms: Gsol=$G_{RF}$+Gwfd+Gnp.

The SCRF algorithm of the present invention is comprised of two steps: (1) calculation of a gas phase; and (2) solving the PB equation for each self-consistent field (SCF) cycle until the solute wave function is self-consistent with the solvent reaction field. The cost of desolvation is estimated by calculating the solvation free energies of the protein, the ligand and the complex.

Absolute scores are calculated, referred to herein as "QMScores," and are compared to experimental binding free energies. Multiple linear regression (MLR) is used to determine the coefficients or weights for each energy contribution that enables a linear interaction energy (LIE) model, which can be used subsequently to compute binding free energies of other inhibitors and or drug molecules.

BRIEF DESCRIPTION OF THE DRAWINGS

Table I shows the effect of minimization of ligand geometries on energy components. (*) shows ligand minimized with Generalized Amber Force-Field parameters; (a) shows outliers from the dataset; and (b) shows non-outliers from the dataset.

Table II shows $K_i$ differences measured in crystallographic and binding assay conditions.

FIG. 3A is a scatter plot of experimental free energy of binding ($\Delta G_{exp}$) versus predicted free energy of binding ($\Delta G_{pred}$) for 150 protein-ligand complexes; FIG. 3B is a scatter plot of $\Delta G_{exp}$ versus absolute score (QMScore) for the same set; FIG. 3C is a scatter plot for $\Delta G_{exp}$ versus $\Delta G_{pred}$ for reduced set of 140 structures; and FIG. 3D is a scatter plot of $\Delta G_{exp}$ versus QMScore for reduced set.

FIG. 4A is a scatter plot of experimental free energy of binding versus predicted free energy for structures lying within one standard deviation of $\Delta HF+\Delta LJ6+\Delta Gsolv$; and FIG. 4B is a scatter plot of experimental free energy of binding versus predicted free energy for structures lying within one half a standard deviation of $\Delta HF+\Delta LJ6+\Delta Gsolv$.

FIG. 5A shows the relationship of resolution of crystal structure with the square of the correlation coefficient; FIG. 5BB shows the relationship of angle energies; FIG. 5C shows the relationship of bond energies; and FIG. 5D shows the relationship of bond energy plus angle energy of complexes to the square of the correlation coefficient.

FIG. 6A shows $\Delta G_{exp}$ versus $\Delta G_{pred}$ for the best 100 complexes from the dataset; and FIG. 6B shows $\Delta G_{exp}$ versus $\Delta G_{pred}$ for best 90 complexes from the dataset.

FIG. 7A shows $\Delta G_{exp}$ versus $\Delta G_{pred}$ for 25 HIV-I protease complexes; FIG. 7B shows $\Delta G_{exp}$ versus QMScore for 25 HIV-1 protease complexes; FIG. 7C shows $\Delta G_{exp}$ versus $\Delta G_{pred}$ for 16 serine protease complexes; FIG. 7D shows $\Delta G_{exp}$ versus QMScore for 16 serine protease complexes; FIG. 7E shows $\Delta G_{exp}$ versus $\Delta G_{pred}$ for 13 human carbonic anhydrase complexes; and FIG. 7F shows $\Delta G_{exp}$ versus QMScore for 13 human carbonic anhydrase complexes.

DESCRIPTION OF THE PREFERRED EMBODIMENTS

Figure 1A:
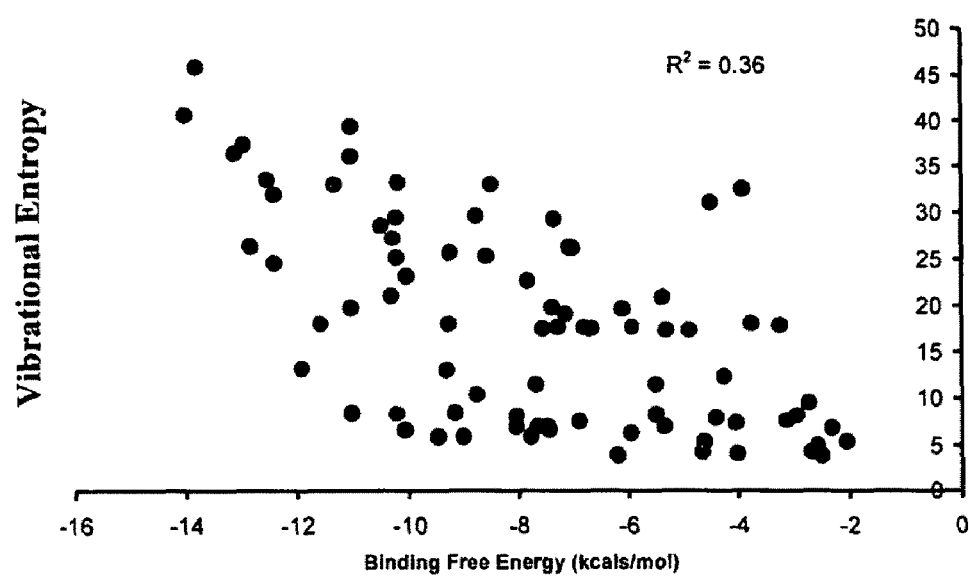
FIG. 1A is the vibrational entropy of 80 ligands from a dataset of protein-ligand complexes plotted against the free energy of binding.

The present invention provides for the first time a quantum mechanics (QM)-based method for scoring complete protein-ligand interactions employing superior levels of quantum mechanical theory for predicting the free energy of binding for protein-ligand complexes. In particular, the present invention provides a linear scaling quantum mechanical [O/(N)] methodology that uses a divide and conquer (D&C) approach and quantum mechanical Hamiltonians and/or quantum mechanical/molecular mechanical (QM/MM) Hamiltonians to predict the free energy of binding of protein-ligand complexes. Quantum mechanical approaches that can be used in the present invention include, without limitation, semiempirical Hamiltonians, Hartree-Fock (HF) (ab initio) Hamiltonians, density functional theory (DFT) and quantum Monte Carlo (QMC) Hamiltonians.

The present invention is the first of its kind to use quantum mechanics to describe the enthalpic and solvation effects in protein-ligand binding. The present method is capable of predicting the free energy of binding within 2 to 2.5 kcals/mol, and may be further refined to enable lead optimization and lead generation in computational drug design.

The QM Hamiltonians that can be used in the present invention routinely and accurately compute a wide range of molecular properties, such as energies, equilibrium geometries, vibrational frequencies, charge distributions, electrostatic properties, magnetic shielding, spin-spin splittings, time-dependent quantities and others, which are not readily available using QM/MM or [O/(N)] methodologies alone.

Both the HF and the DFT approaches can be used to understand metalloproteins by their ability to reproduce the internal forces of the first-shell ligands around the metal centers of the proteins that, in turn, primarily determine the structure of the active site complex. Thus, a variety of possible intermediates and transition states can be identified using a metalloenzyme active site model that differs only by the placement of protons and/or water molecules, the coordination environment, the oxidation state of the metal centers and so on. In such a complex scenario, a systematic QM investigation of cluster models can help to discriminate among proposed mechanisms of protein-ligand interaction. In those cases in which a complete determination of the reaction pathway is still not computationally feasible, a molecular mechanical approach of the ground-state QM data can give information about the possible reaction coordinates for protons, electrons, substrates and products.

The combined QM/MM simulations of the present invention provide a powerful means to study QM processes in protein-ligand interactions in a solvent environment. This approach exploits the fact that protein-ligand interactions that require a QM treatment, such as bond formation and bond breaking, are usually confined to a small region of the active site of the protein. This region, which typically consists of up to a few tens of atoms, is described by semiempirical, DFT or HF (ab initio) Hamiltonians, whereas the remainder of the system is described by a classical molecular mechanical (force-field) Hamiltonian. The interaction between the QM and classical MM regions usually is described by a combination of electrostatic and van der Waals interactions.

In studying the quantum-mechanical properties of solids, the underlying physical laws have been known for over 70 years. The difficulty arises from the complexity of the equations that, as Dirac in 1929 (Dirac, P. A. M, Proc. R. Soc. London, Ser. A, 123, 714, 1929) famously wrote, are "much too complicated to be soluble." With current parallel computers, however, periodic systems containing up to a thousand or so electrons, which is enough to model many properties of solids with high accuracy, can be simulated.

The HF (ab initio) approach is well known in the art and is the simplest theory that correctly incorporates the permutation symmetry of the wave function. "Ab-initio" is a term used to describe an accurate (though not exact for anything other than the hydrogen atom) solution of the non-relativistic, time independant Schrödinger equation: $\hat{H}\Psi=E\Psi$, where $\hat{H}$ is the Hamiltonian operator for the system, a function of kinetic and potential energies of the particles of the system, $\Psi$ is the total molecular wavefunction, and E is the molecular energy. It is computationaly impossible to solve this equation for anything other than the hydrogen atom. For this reason, for a many bodied system, approximations are introduced to simplify the calculations. One of these approximations is that of Born and Oppenheimer, where the approximation consists of the assumption that, because electrons travel much faster than nuclei, the electrons are viewed as travelling in a potential generated by a stationary nucleus. This approximation allows the electronic Hamiltonian to be considered for a fixed set of nuclear coordinates.

Another computational method that can be used in the present invention is based on density-functional theory, which is the most popular approach for calculating the electronic properties of solids and large molecules. DFT is a formally exact theory based on a theorem of Hohenberg and Kohn (Hohenberg, P. and W. Kohn, Phys. Rev. 136, B864, 1964), which states that the ground-state properties of a many-electron system may be obtained by minimizing the functional $E[n(r)]$ of the electron number density $n(r)$. The minimum value of the functional is the exact ground-state energy, and the minimum is attained when $n(r)$ is the exact ground-state density. Computational use of DFT is well known and is used in the fields of physics, chemistry, biochemistry, materials science, geophysics, as well as in the pharmaceutical industry for drug design.

The QMC computational approach has become a valuable tool known in the art for calculating the physical properties of solid materials. The term "QMC" covers several different techniques based on random sampling. The simplest of the techniques, variational Monte Carlo (VMC), uses a stochastic integration method to evaluate expectation values for a chosen trial wave function, in which the accuracy of the technique depends on the accuracy of the trial wave function. Another technique is diffusion Monte Carlo (DMC), which overcomes the limitation of VMC by using a projection technique to enhance the ground-state component of a starting trial wave function. Both VMC and DMC methodologies are approaches contemplated for use in the present invention.

In one embodiment of the present invention, a method is provided that includes a linear scaling technique which uses a divide and conquer (D&C) approach and semiempirical Hamiltonians for solving large molecular systems quantum mechanically. The D&C approach is implemented via a computer program referred to as DIVCON. This program is coupled to a Poisson-Boltzmann (PB)-based self-consistent reaction field (SCRF) method for calculating the free energy of solvation, which accounts for the perturbation of the gas-phase Hamiltonian in response to a dielectric. The calculated binding affinities are compared to experimental values to measure the success of the method. Heats of formation of molecular systems with up to five thousand atoms can be calculated in a reasonable amount of time.

The present invention may be enhanced by refining the starting geometries of the complexes using molecular mechanics and/or quantum mechanics methods so that noise can be eliminated from the dataset, and exploring the binding energy landscape of the ligand in the active site of the protein by generating different poses of the ligand in the active site and investigating its relationship with the predictive capability of the scoring function. This can be achieved by using docking algorithms such as DOCK, AUTODOCK and FlexX to generate the poses and calculate different energy components using the method described herein. A database of misdocked "decoy" structures can be used to validate whether the novel scoring function of the present invention is able to discriminate between correct poses (low root mean squared deviation (RMSD) from the x-ray structure) and incorrect poses (high RMSD from the x-ray structure).

In addition to the quantitative model, a qualitative model based on the inventors' divide and conquer (D&C) energy decomposition scheme is employed to compute electrostatic, polarization and charge transfer components of the interaction energy of a ligand with a protein. Moreover, ligands can be broken down into small parts and the same quantities for the individual synthons or user-selected pieces of the ligand can be determined. These quantities may in turn be used to identify groups that contribute favorably or unfavorably to binding. This energy decomposition scheme gives novel insights into key aspects of the interaction between a ligand and a protein, as well as insights into the importance of quantum mechanical effects like polarization and charge transfer in protein-ligand interactions relative to electrostatic interactions.

In particular, the method comprises downloading protein-ligand complexes from a Protein Data Bank (PDB). Protons are added to heavy atoms of each protein using the LEAP module of AMBER 5.0 (Case, D. A. et al., AMBER, version 5.0; University of California, San Francisco, Calif., 1997). All heavy atoms are fixed at the experimental coordinates during energy minimization. The active site of the uncomplexed protein is modeled with a zinc-bound water molecule. The interaction energy is calculated using the thermodynamic cycle, as shown in FIG. 1. In particular, the solution-phase free energy of binding ($\Delta G_{bind}$) is decomposed into a gas-phase interaction energy ($\Delta G_b^g$) and a solvation free energy ($G_{sol}$). The gas phase interaction energy is the sum of enthalpic energy ($\Delta H_b^g$) and entropic energy ($\Delta S_b^g$). The quantum mechanical part of $\Delta H_b^g$ is calculated using DIVCON (Dixon, S. L. et al., DIVCON; The Pennsylvania State University, University Park, Pa., 1999) at the AM1 level (Dewar, M. J. S. et al., J. Am. Chem. Soc., 107:3902-3909, 1985) as $\Delta H_f=\Delta H_f(\text{complex})-\Delta H_f(\text{protein})-\Delta H_f(\text{ligand})$. The dispersive part of the nonpolar interaction is calculated using the attractive part of the Lennard-Jones potential using the AMBER 96 force-field [$(1/R^6)$LJ] (Cornell, W. D. et al., J. Am. Chem. Soc., 117:5179-5197, 1995). The entropic contribution to binding ($\Delta S_g$) is described by a solvent and conformational component. The solvent entropy, which is gained by water on being displaced from the active site by the ligand during binding, is estimated based on the surface area burial for carbon, oxygen, nitrogen, and sulfur atoms during binding. The conformational entropy is evaluated from the number of degrees of freedom that is lost in the low molecular weight molecule and side chains in the active site during binding [(num(rot_bonds)]. A value of 1.0 kcal/mol is used for the loss of a rotatable bond. The free energy of solvation is evaluated using the Poisson-Boltzmann/self-consistent reaction field (PB/SCRF) method (Gogonea, V. et al., J. Phys. Chem. A, 103(26):5171-5188, 1999). CM2 charges (Li, J. B.

et al., J. Phys. Chem., 102:1820-1831, 1998) are used in the PB/SCRF calculation. Thus, the final total score, i.e., free energy of binding ($\Delta G_{bind}$), is the sum of $\Delta G_b{}^g$ and ($\Delta G_{solv}{}^{protein-ligand} - \Delta G_{solv}{}^{protein} - \Delta G_{solv}{}^{ligand}$).

The predictive capability of this method for scoring protein-ligand interactions is a plot of the experimental binding free energy ($\Delta G_{exp}$), calculated as $-RT \ln K_i$ versus the calculated total score. The standard error is calculated as:

$$\text{Std.Error} = \sqrt{(\Delta G_{exp} - (mTS+c))^2}$$

where $mTS+c$ is the equation of the line fitted to $\Delta G_{exp}$ and TS is the total score.

All protein and ligand atoms are assigned atomtypes in order to calculate internal and non-bonded interaction energies. Protein heavy atoms are assigned atomtypes based on the AMBER 96 force-field. Ligand heavy atoms are assigned atomtypes using the antechamber module of the AMBER 7.0 suite of programs. Antechamber uses the generalized amber force-field (gaff) for assigning atomtypes (J. Wang et al., Development of a General Amber Force-Field, 2003). Since protons assigned to the ligand and protein heavy atoms are in standard geometries, a very high restraint (~5000 kcals/mol) is placed on the heavy atoms, and hydrogen atom positions are optimized in the complex using the AMBER 6.0 program. Five hundred cycles of steepest descent are followed by 2500 cycles of conjugate gradient energy minimization. The complex is then taken apart, and hydrogen atom positions are re-optimized in the protein and ligand in the absence of each other. Quantum mechanics calculations then are performed on these structures.

The free energy of solvation ($G_{sol}$), with respect to binding plays an important role in binding and, as used herein, is the desolvation of the ligand and the active site of the protein during the process of docking. The solvation free energy is the difference between the solute free energy in solution and the gas phase. In solution, the charge distribution on the free ligand is polarized by the solvent dielectric, whereas in the bound state its charge distribution changes in response to the dielectric in the protein. These effects, while hard to capture by classical methods, are suited perfectly for QM methods. In the case of a quantum mechanical description of the solute, the solvation free energy can be decomposed into a sum involving the reaction field (electrostatic $G_{RF}$), solute wave function distortion (Gwfd) and a hydrophobic (Gnp) term:

$$Gsol = G_{RF} + Gwfd + Gnp$$

$G_{RF}$ is calculated from the interaction of protein or ligand charge density with the electrostatic potential generated by the reaction field:

$$G_{RF} = \tfrac{1}{2}\int_V \rho(r)\phi_{RF}(r)dr$$

where $\phi_{RF}(r)$ is the electrostatic potential and $\rho(r)$ is the solute charge density.

The use of the Poisson-Boltzmann (PB) approach has the advantage of representing the dielectric discontinuity by assigning different dielectric constants to the solute and the continuum solvent. Most of the information necessary to evaluate the solvation free energy is given by this discontinuity in the dielectric. An alternative to the use of the electrostatic potential for the evaluation of the reaction field energy is to use an appropriate virtual surface charge density ($\sigma_{RF}$) placed at the dielectric interface, which generates the reaction field potential. Thus, the surface charge density and not the reaction field itself is used to evaluate the reaction field free energy:

$$G_{RF} = \frac{1}{2}\int_V dr \rho(r) \int_S dr' \frac{\sigma_{RF}(r')}{|r-r'|}$$

Gnp contains contributions from cavity formation and solvent-solute dispersion interactions, and for low molecular weight molecules these two terms typically are taken together (and called nonpolar or hydrophobic) and are considered to be proportional to the molecular or solvent-accessible surface area:

$$G_{np} = \sum_i \tau_i A_i$$

where $A_i$ is the surface area of one solute atom and $\tau_i$ is a surface tension parameter specific for that atom.

When the solute is described quantum mechanically, the reaction field potential polarizes its charge distribution (i.e., distorts the gas phase wave function), and this is taken into account by perturbing the gas-phase solute Hamiltonian, $H^0$, with a potential energy operator coming from the interaction of the virtual surface charges with solute electrons and nuclei:

$$H = H^0 + \int_S da' \frac{\sigma(r')}{|r-r'|}$$

As used herein, da' is an area element of the solute surface (S). Thus, the construction of the solute wave function in solution has to be carried out self-consistently with the generation of the reaction field (the so-called SCRF method), i.e., the surface charges. Thus, the solute energy solution is given as:

$$E = \left\langle \Psi \middle| H^0 + \int_S da' \frac{\sigma(r')}{|r-r'|} \middle| \Psi \right\rangle + E_{nucl} + \sum_i^{N_{SC}} \sum_A^{N_{at}} \frac{Z_A \sigma_i}{|r_i - r_A|}$$

where $\sigma_i (=\int_S da' \sigma(r'))$ is the surface charge obtained by integrating the surface charge density ($\sigma(r')$) over an element ($dS_i$) of solute surface area, ($N_{Sc}$) the number of surface charges, and ($N_{at}$) the number of solute atoms. The last two terms are the core-core repulsion and core-surface charge interaction, respectively.

The SCRF algorithm of the present invention comprises two steps: first, a gas phase calculation is performed (with or without geometry optimization). This is necessary to evaluate the energy due to solute polarization; and second, the PB equation is solved for each self-consistent function (SCF) cycle until the solute wave function is self-consistent with the solvent reaction field. When finite difference methods (FDMS) or finite element methods (FEMs) are used to solve the PB equation, the electrostatic potential is first determined as the solution of the PB equation and then the surface charges are obtained from the discontinuity in the electric field at the dielectric boundary. When the boundary element method (BEM) is used to solve the PB equation, the virtual surface charges (VSC) are obtained at the start.

The calculation of solute energy in solution by means of the effective Hamiltonian using any VSC-based approach requires the evaluation of one-electron terms (which contain the contribution from the reaction field). A peculiarity of semiempirical methods is that the one-electron integral Fock terms and core-core repulsion terms are evaluated by using two-electron repulsion integrals. Consequently, the surface charge-electron interaction terms and the core-surface charge terms also are evaluated using two-electron integrals (in the same way that electron-core interactions are calculated).

Briefly, the virtual surface charges ($\sigma_i$) are given a core status; hence, hydrogenoid s-type orbitals are centered on these surface charges in order to calculate the two-electron repulsion integrals necessary to evaluate the one-electron and surface charge-core terms which add the solvent contribution to the solute Hamiltonian. Thus, the SCRF energy is:

$$E_{RF} = \sum_{i}^{N_{SC}} \sigma_i \left( \sum_{A}^{N_{at}} \frac{Z_A}{|r_i - r_A|} - \left\langle ss \left| \frac{1}{|r_i - r|} \right| \psi \right\rangle \right)$$

where $r_i$ is the position of surface charge $\sigma_i$ and $r_A$ the position of atom A. The core-surface charge term (the first term) has a Coulomb type form, but the actual semiempirical implementation uses a two-electron integral-based formula over s-type orbitals.

The divide-and-conquer (D&C) method implemented by DIVCON is a linear scaling algorithm for solving the Schrodinger equation for large molecules. The D&C method involves dividing the entire molecule into subsystems and replacing the diagonalization of the Fock matrix for the whole molecule (which scales as $N^3$, where N is the number of basis functions) with a series of subsystem diagonalizations. This approach originated in the observation that the basis functions used to expand the molecular orbitals are localized, consequently the Fock matrix for large molecules is sparse. The D&C method is equally applicable to both localized and delocalized species, but works more effectively with the former. Following this partitioning, as many subsystem Fock equations as subsystems are obtained:

$$F^\alpha C^\alpha = C^\alpha E^\alpha, \alpha = 1, \ldots, n_{sub}$$

As a consequence, the density matrix for the whole molecule, $P_{\mu\nu}$, can be written as a sum of the density matrixes of the subsystems $P_{\mu\nu}^\alpha$:

$$P_{uv} = \sum_{\alpha=1}^{n_{sub}} D_{\mu\nu}^\alpha P_{\mu\nu}^\alpha$$

The factor $D_{\mu\nu}^\alpha$ is assigned a value of 0 or $1/n_{\mu\nu}$ (where n is the number of times basis function $\mu$ and $\nu$ appear; generally this term is equal to 1) in order to mask out particular density matrix elements. The subsystem density matrix $P_{\mu\nu}^\alpha$ in turn is built by introducing an occupation number $n_i^\alpha$:

$$P_{\mu\nu}^\alpha = \sum_{i}^{MOs} n_i^\alpha (c_{\mu i}^\alpha) * c_{\nu i}^\alpha$$

which is calculated according to a protocol proposed by Yang and Lee (J. Chem. Phys. 103:5674-5678, 1995):

$$n_i^\alpha = 2/(1 + \exp[(\in_i^\alpha - \in_F)/kT])$$

where k is a Boltzmann constant and T is absolute temperature; the actual value of T has little effect on the calculation unless a very large value is chosen. $\in_i^\alpha$ is the energy eigenvalue of the i "molecular orbital" in subsystem $\alpha$ and $\in_F$ a Fermi energy level (an adjustable quantity), whose value is determined from the normalization condition on P, i.e., the total number of electrons in the system is conserved. Within the semiempirical framework, this condition involves only the diagonal elements of P:

$$n_{elec} = \sum_{\mu}^{N} \sum_{\alpha}^{n_{sub}} D_{\mu\mu}^\alpha \sum_{i}^{MOs} n_i^\alpha |c_{\mu i}^\alpha|^2$$

Because $P^\alpha$ depends one $\in_F$, it cannot be assembled until Roothan-Hall equations have been solved for all subsystems:

$$F^\alpha C^\alpha = S^\alpha C^\alpha E^\alpha$$

where $C^\alpha$ is the subsystem coefficient matrix, $F^\alpha$ is the subsystem Fock matrix, and $E^\alpha$ is the diagonal matrix of orbital energies for subsystem $\alpha$. $S^\alpha$ is the overlap matrix, which is equal to the identity matrix for the semiempirical Hamiltonian. In practice, $\in_F$ from the previous SCF cycle is used to determine the subsystem density matrices.

The present invention couples the D&C algorithm to the PB equation. The PB equation accounts for solvent screening and salt effects and is usually cast in the following two forms (nonlinear/linear):

$$\nabla \cdot [\in(r) \nabla \phi(r)] - k(r)^2 \sin h(\phi(r)) = -4\pi \rho(r)$$

$$\nabla \cdot [\in(r) \nabla \phi(r)] - k(r)^2 \phi(r) = -4\pi \rho r$$

where $\phi(r)$ is the electrostatic potential at position r, $\in(r)$ is the dielectric constant, $k(r)$ is a modified Debye-Huckel parameter, and $\rho(r)$ is the solute charge density. The PB equation allows for 1 analytical solutions for only a few regular shapes, e.g., sphere, cylinder, and only numerical solutions are possible for molecules with complicated shapes.

The increase in computer power (both in speed and memory) over the last few decades has stimulated the development of high-performance algorithms for solving the PB equation for molecules of biological interest. Thus, several mathematical techniques typically used for solving partial differential equations have been developed, such as the finite difference method (FDM), the finite element method (FEM) and the variational method (VM). Another mathematical technique, known as the boundary element method (BEM), does not solve the PB equation directly, but provides the same answer as far as the Poisson equation is concerned, i.e., it is equivalent to solving the Poisson equation directly for the electrostatic potential.

The divide and conquer/Poisson-Boltzmann (D&C/PB) coupling of the present invention uses the finite difference method (FDM) to solve the PB equation, as implemented in the DelPhi program of Honig et al. (J. Comp. Chem., 12:435-445, 1991), which is incorporated herein by reference.

DIVCON calculates the gas phase heat of formation of a molecule, which comprises the electronic energy and the core-core repulsion. The interaction energy is thus the difference in the heat of formation of the complex, i.e., the protein-ligand complex. DIVCON does not capture the attractive part of the nonpolar interaction. In order to account for this interaction, the attractive ($1/R^6$) portion of the Lennard-Jones interaction energy is calculated using the AMBER 96 force-field algorithm for non-bonded atoms. The enthalpic contribution to the gas-phase interaction energy is therefore the sum of the heat of formation and the attractive portion of the Lennard-Jones interaction.

As used herein, the entropic energy ($\Delta S$) contribution to binding can be described by a conformational component and a solvent component. The solvent entropy is the entropy gained by water molecules on being displaced from the active site by the ligand during binding. This is quite difficult to calculate accurately, and requires extensive molecular dynamics simulations of the protein in solvent. Because it is believed that solvent entropy depends on the changes in the polar and apolar exposed surface area of the protein during binding, the present invention includes estimating the solvent entropy based on these changes in the protein's polar and apolar exposed surface area. The conformational entropy is evaluated from the number of degrees of freedom that are lost in the active site during binding. Typically, conformational entropy in scoring functions is calculated by counting the number of rotatable bonds in the ligand molecule. This method, however, only accounts for the degrees of freedom lost by the ligand. In the process of binding to a ligand, the exposed amino acid side chains in the active site of a protein also loses conformational entropy when it is locked in a particular conformation with the ligand. Therefore, the method of the present invention also includes adding as a descriptor the rotatable bonds present in the protein side chains in the active site, as well as the rotatable bonds in the ligand. Although this provides a simplistic approximation for conformational entropy, this approximation is used because free energy of binding is calculated by examining the properties of a single three-dimensional structure. A more accurate evaluation of the entropy of binding requires a normal mode analysis and is impractical for scoring such large datasets.

The cost of desolvation then is estimated by calculating the solvation free energies of the protein, the ligand and protein-ligand complex.

The master equation used to calculate the free energy of binding, therefore, is a linear combination of the different components, described as follows:

$$\Delta Gpred = f(\Delta H, \Delta Gsolv, T\Delta S)$$

$$\Delta H = \alpha(\Delta HF) + \beta(\Delta LJ6)$$

$$\Delta Gsolv = \gamma(\Delta Gsolv)$$

$$T\Delta S = \delta(\Delta polarSA) + \varepsilon(\Delta apolarSA) +$$
$$\{[\phi(\text{rotatable\_bonds})]\text{OR}$$
$$\left[S_{vib} = R\sum_{j=1}^{3n-6} \frac{\Theta vj/T}{e^{\Theta vj/T} - 1} - \ln(1 - e^{-\Theta vj/T})\right]\}$$

where, $\Delta Gpred$ is the predicted or calculated free energy of binding, $\Delta H$ is the enthalpy, $\Delta HF$ is the heat of formation portion of the interaction energy, $\Delta LJ6$ is the attractive portion of the nonpolar interaction energy, and $\Delta Gsolv$ is the solvation/desolvation free energy. $T\Delta S$ is the entropy of binding, related to $\Delta polarSA$, which is the polar surface area of the protein lost due to binding, and $\Delta apolarSA$ is the apolar surface area lost during binding. The last term can be either the number of rotatable bonds that are locked in the active site during binding, or vibrational entropy ($S_{vib}$). The above-described terms all are related to the free energy of binding ($\Delta G_{bind}$).

The entropy of binding (T$\Delta$S) can be described by a conformational component and solvent component. Conformational entropy is difficult to estimate accurately without exhaustive enumeration of all of the conformers of the ligand, the protein and the complex. Such exhaustive enumeration is intractable in the framework of a typical QM scoring function. The number of rotatable bonds, however, is a common used technique in the art for measuring conformational entropy for a variety of scoring functions. The rationale for using rotatable bonds is that rotatable bonds is a measure of the frozen degrees of freedom in binding and thus they reflect the loss of conformational entropy. The present inventors have studied conformational entropy at various levels. For example, the number of rotatable bonds in a ligand can be used as a first approximation. A higher order approximation for conformational entropy can be implemented by carrying out normal mode analysis on the ligand at the QM level. Frequencies can be calculated at the AM1 and PM3 level using semiempirical quantum theory and the D&C approach. Prior to calculating frequencies, geometry optimization of the ligand to convergence can be performed using the LBFGS minimization algorithm protocol, a protocol which is well known by those skilled in the art. The vibrational entropy $S_{vib}$ then is calculated from the resultant frequencies using the following expression:

$$S_{vib} = R\sum_{j=1}^{3n-6} \frac{\Theta vj/T}{e^{\Theta vj/T} - 1} - \ln(1 - e^{-\Theta vj/T})$$

where R is the gas constant and $\Theta vj$ is the vibrational temperature calculated from the frequencies of the 3n-6 normal modes for the molecular system at standard temperature T.

Figure 1B:
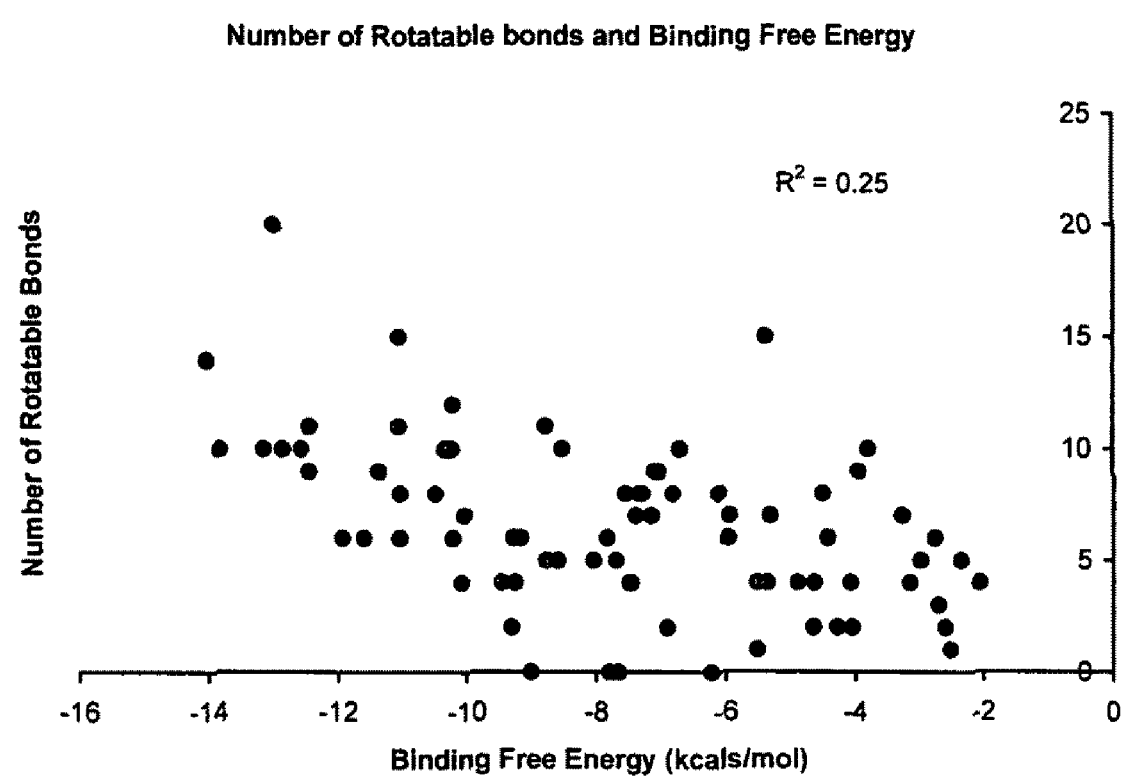
FIG. 1B is the number of rotatable bonds plotted against the free energy of binding.
Figure 2:
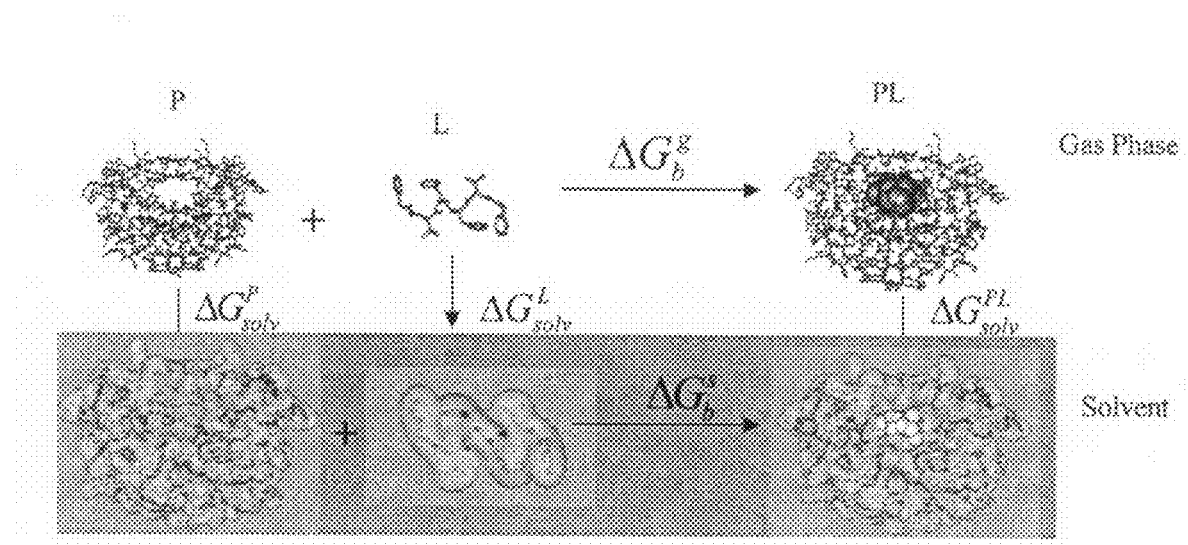
FIG. 2 is an illustration of the thermodynamic cycle used to calculate the free energy of binding of ligand to protein.

Calculation of the vibrational entropy of a ligand using QM in order to predict the free energy of binding of protein-ligand interactions of the present invention better correlates with the free energy of binding of a protein-ligand complex than calculating the number of rotatable bonds, which has been the typical way to estimate conformational entropy of a ligand fused in empirical and knowledge based scoring functions. As shown in FIG. 1A, the vibrational entropy of 80 ligands from a dataset of protein-ligand complexes is plotted against the free energy of binding. The square of the correlation coefficient is 0.36 (correlation coefficient of 0.6). As shown in FIG. 1B, the number of rotatable bonds is plotted against the free energy of binding. The square of the correlation coefficient is 0.25 (correlation coefficient of 0.49). The higher correlation coefficient achieved by vibrational entropy calculations demonstrates the superior predictive ability of using vibrational entropy in a quantum mechanical protocol over a simple rotatable bonds term. Typically, other scoring functions parameterize the type of rotatable bonds in order to achieve a higher correlation with experimental values. Because the scoring function of the present invention is physically based, such parameterization, which is highly dependent on a dataset, is not required.

Further, the present invention contemplates estimating the difference in vibrational entropy of a ligand due to its binding to its substrate protein, by performing normal mode analysis of the ligand in the protein and in the solvent. This can be achieved by performing geometry optimization of the protein-ligand complex using a semiempirical Hamiltonian and then calculating the vibrational entropy of the ligand in the active site of the protein. The difference in the vibrational entropy of the ligand in the active site and in the solvent can then be calculated.

Absolute scores are calculated, referred to herein as "QMScores," and compared to experimental binding free energies. As used herein, the QMScore is the sum of all the above terms except for the number of rotatable bonds [$\phi$(rotatable_bonds). The relative weights of the different energetic components are unknown, however, and the experimental values span a relatively narrow range of free energy (−2 to −14 kcals/mol). Thus, multiple linear regression (MLR) is used to determine the coefficients or weights ($\alpha$ through $\phi$) for each of the individual terms. Regression methods seek to minimize the error between a dependent variable and independent variables in a least squares way and typically are used to compute weights of various energy terms in scoring functions. MLR thus enables the construction of a linear interaction energy (LIE) model having various energy terms and coefficients that subsequently can be used to evaluate drug candidates by computing the binding free energies of other protein-ligand complexes, wherein the proteins include, without limitation, protein receptor molecules, and the ligands include, without limitation, inhibitors, agonists or other low molecular weight molecules.

In another embodiment of the present invention, the linear scaling ability of the density matrix divide and conquer (D&C) algorithm is leveraged by implementing the algorithm in parallel. This reduces the time needed to perform semiempirical calculations to a point where it is feasible to perform molecular dynamics using a fully semiempirical Hamiltonian. The partitioning scheme of the D&C algorithm, in which the entire system is split into many smaller subsystems, is used to implement the algorithm in parallel, i.e, individual subsystems are distributed across processors in a parallel machine. In this manner, the scaling of performance on a parallel machine is limited only by the time required to diagonalize the Fock matrix of the largest subsystem.

A replicated data strategy is used for parallel implementation because of its simplicity and ease of implementation. Although replicated data implementations of parallel programs normally do not scale very well to large numbers of processors, a small number of processors, typically in the range of about 30 to 70, are employed to accomplish the calculations. Another important limitation of the replicated data strategy is available memory, in that each processor must instantiate all variables of the entire program, which limits the size of systems that can be used to the size that will fit on a single processor. The serial implementation of the D&C algorithm is very memory efficient and can accommodate several thousand atom systems on a workstation with only 32 Mb of memory. The cutoff employed in the D&C algorithm linearizes the storage requirements. Based on the above, calculations on systems of over 10,000 atoms can be carried out on most parallel machines.

The main features of parallel implementation are typical of any replicated data program, and has been previously described by The MPI Forum (University of Tennessee, Knoxville, Tenn., 1993); Foster, I. *Designing and Building Parallel Programs: Concepts and Tools for Parallel Software Engineering*. Addison-Wesley, Reading, Mass., 1995); Brode, S. et al. (J. Comp Chem., 14:1142, 1993); Feyereisen, M. et al. (Theor. Chim Acta 84:289, 1993); Pettersson, L G M et al. (Theor. Chim Acta 85:345, 1993); and Furlani et al. (J. Comp Chem., 16:91, 1995), which are incorporated herein by reference. Additionally, much research has been devoted to general methods for parallel matrix diagonalizations due to their necessity in many scientific programs.

The present invention provides a variation of parallel implementation that avoids parallel diagonalization altogether by breaking up the work across processors at a level above the diagonalization itself, i.e., each processor completes a diagonalization of the local Fock matrix for one or more subsystems. An advantage of this method is that the superior performance of native serial diagonalization routines on many machines can be exploited. Load balancing of subsystems across processors is carried out with a simple Greedy algorithm that uses the number of orbitals in a subsystem and completion time per subsystem to balance the work load efficiently across processors. The algorithm treats subsystems as units of work of varying size and distributes them across processors in such a way that each processor has an equal share of the total work. The optimal load balance achieved is normally not a perfect balance because most often the work cannot be divided exactly among processors. In the limiting case, a single processor is assigned one subsystem, the largest subsystem in the calculation. A simplified pseudo code Greedy algorithm is shown below.

```
Greedy load balancing:
sort subsystems in decreasing order
determine target solution
for i = 1, number_subsystems
    For j = 1, number_pe's
        if (FEASIBLE(my_solution,i)) then
            my_solution = UNION(my_solution, i)
        endif
    end
end
```

The first step of the algorithm sorts a list of all subsystems by size, using either the number of orbitals in that subsystem, or the completion time for diagonalization of the local Fock matrix. In a second step, a target solution based on the measurement used in the first step is computed by dividing the total work to be performed by the number of processors. For example, if the sum of completion times of all subsystems is 1000 s, then on 8 processors the target would be 1000/8. This is equal to the amount of work each processor ideally can implement. In the loop that follows, subsystems are assigned to processors, with the condition that each processor must not exceed the target value when a subsystem is assigned to that processor. The FEASIBLE routine checks for this condition. If FEASIBLE returns true, the subsystem is added to that processor's pool of subsystems (UNION (my_solution,i)). If not, the next processor is checked. If all processors exceed the target value, the subsystem is assigned to the processor with the lowest work total at that point.

The first iteration of an SCF cycle uses the number of orbitals in a subsystem for sorting and as the selection criterion in the FEASIBLE routine. The second iteration uses actual completion times. Subsystem distribution among processors then is left in the balanced state until a new SCF cycle begins. Load balancing is performed once in a single point calculation, and once at the start of each new SCF cycle in a geometry optimization. During geometry optimization, subsystems can be regenerated. Any new distribution of atoms among subsystems requires load balancing.

The present invention is more particularly described in the following example, which is intended to be illustrative only, because numerous modifications and variations therein will be apparent to those skilled in the art.

Example 1

Calculation of Protein-Ligand Binding Free Energy Method

One hundred and fifty protein-ligand complexes were downloaded from a Protein Data Bank (PDB), in which each complex's three-dimensional structure and experimental Ki's, Kd's, IC50's and/or binding free energies had been experimentally determined. Binding measurements were converted to a free energy value using the Gibbs equation ($\Delta G=-RT \ln Ki$). A list of the structures along with their PDB ID and binding free energies is provided in Table I. The PDB database comprised protein families that include, without limitation, aspartic proteases, serine proteases, sugar binding proteins, amino acid binding proteins or carbonic anhydrases. The protein-ligand complexes were characterized by a wide spectrum of active site structures and chemical patterns. The structures also spanned a wide range of experimental binding affinities from −2 kcals/mol to −14 kcals/mol.

Preprocessing of the protein-ligand structures from the PDB files was accomplished as follows. Heteroatoms not in the active site, such as metals and ion, as well as water, were removed from the PDB file. The proteins and ligands were extracted from each PDB file and heavy atoms of the proteins and ligands were protonated. Protonation of protein heavy atoms was performed using the LEAP module of the AMBER 6.0 suite of programs, and protons were assigned to heavy atoms based on standard geometries. Protonation of ligand heavy atoms was more challenging because of the lack of a standardized procedure for such protonation. A combination of PRODRUG (D. M. F. van Aalten, et al. "PRODRUG, J. Comput. Aided Mol. Des., 10:255-262, 1996), BABEL and a program developed by the present inventors was used to automate assignment protons to the heavy atoms in the ligands. In the event of conflicting protonation states, the ligand structures were visually inspected and the heavy atoms were assigned protons.

All protein and ligand atoms were assigned atomtypes in order to calculate internal and non-bonded interaction energies. Protein heavy atoms were assigned atomtypes based on the AMBER 96 force-field. Ligand heavy atoms were assigned atomtypes using the antechamber module of the AMBER 7.0 suite of programs. Antechamber uses the generalized amber force-field (gaff) for assigning atomtypes (J. Wang et al., Development of a General Amber Force-Field, 2003). Because protons assigned to the ligand and protein heavy atoms were in standard geometries, a very high restraint (~5000 kcals/mol) was placed on the heavy atoms, and hydrogen atom positions were optimized in the complex using the AMBER 6.0 program. Five hundred cycles of steepest descent were followed by twenty-five hundred cycles of conjugate gradient energy minimization. The complex then was taken apart, and hydrogen atom positions were re-optimized in the protein and ligand in absence of each other. Quantum mechanical calculations then were performed on these structures, in which a thermodynamic cycle was used to calculate the free energy of binding of the ligand with the protein, as shown in FIG. 1.

The interaction energy in the gas phase was decomposed into enthalpic and entropic contributions. The enthalpic component was in turn decomposed into electrostatic and nonpolar parts. The electrostatic part of the interaction energy was calculated using the semiempirical divide and conquer (D&C) quantum mechanics program DIVCON at the AM1 level of theory. Because the attractive part of the nonpolar interaction is not estimated by DIVCON, the attractive part of the Lennard-Jones potential [AMBER 96 (Case 1997) LJ parameter set] was used to estimate this interaction. The enthalpic part of the complexation energy was thus calculated as a difference in the sum of electronic energy, core-core repulsion and attractive ($R^6$) part of the Lennard-Jones (LJ6) interaction of the ligand and protein from that of the complex.

The entropic part of such an interaction comprises solvent entropy and conformational entropy. The solvent entropy was estimated from the difference in the polar and apolar surface area during binding. The surface areas were calculated using a probe radius of 1.4 A° and standard atomic radii. The conformational entropy was estimated from the number of freely rotatable bonds both in the protein and ligand that were frozen during the process of binding. The number of freely rotatable bonds in the ligand were estimated from the atomtypes and bond order of all the bonds in the ligand. All non-terminal sp3-sp3 and sp3-sp2 bonds involving heavy atoms were considered rotatable. Bonds in aliphatic rings and those involving hydrogen atoms were not included. For the protein only, those amino acid residues that were solvent-exposed in the unbound state, but buried in the complex, were tabulated. Freely rotatable bonds were then assigned, based on the number of rotatable bonds in such amino acid residues. Solvation and desolvation components of the free energy of binding were estimated using the Poisson-Boltzmann based self-consistent reaction field approach implemented in the computer program DIVCON. Both the electrostatic and nonpolar parts of the free energy of solvation were calculated using this method.

Results:

FIG. 3A is a scatter plot of predicted free energy of binding for all 150 complexes versus the experimental binding free energies. The square of the correlation coefficient ($R^2$), which is one of the measures of the success of prediction, was 0.25. The root mean squared error (RMSE) of prediction for this dataset was 2.63 kcals/mol and the Spress was 2.68 kcals/mol. FIG. 3B is a scatter plot of the raw score or QMScore versus the experimental free energies, which shows that the method is capable of capturing the general trend despite the presence of major outliers.

An analysis of the data leads to the conclusion that a reason for poor prediction is the presence of structural outliers that add noise to the dataset. Quantum mechanics calculations are very sensitive to accurate starting geometries of the ligand-protein complex, and the heavy atoms of the proteins and ligands were not optimized in the dataset. Based on the QMScore, a portion of the outliers were excluded from the dataset. FIGS. 3C and 3D show the scatter plots of the predicted free energy and QMScore against the experimental free energy. The square of the correlation coefficient for this set of 140 structures was 0.35 for $\Delta G_{pred}$ and 0.34 for the QMScore.

The sum of $\Delta HF$, $\Delta J6$ and $\Delta G_{solv}$ also was used to screen outliers. This term captures the interaction energy and the desolvation effects. The mean of this quantity ($\Delta HF+\Delta LJ6+\Delta Gsolv$) was −44.17 3 kcals/mol with a standard deviation of 113.72 kcals/mol. FIG. 4A is a plot showing complexes of the dataset with $\Delta HF+\Delta J6+\Delta Gsolv$ lying within one standard deviation of the distribution, i.e., greater than −157 kcals/mol and less than 70 kcals/mol. The square of the correlation coefficient ($R^2$) for this set was 0.42 with Spress of 2.44 kcals/mol. This screened set has 121 complexes with the experimental free energies spanning from −2 kcals/mol to −14 kcals/mol. FIG. 4B is a similar plot, but the complexes included in this dataset layed within half a standard deviation of the distribution, i.e., greater than −100 kcals/mol and less than 12 kcals/mol. The $R^2$ for this set, which had 106 structures, was 0.44 and Spress was 2.25 kcals/mols.

Also inspected was the relationship between the geometries of the protein-ligand complexes and the goodness of fit. FIG. 5A shows the relationship between the square of the correlation coefficient and the resolution of the crystal structures of the complexes. The quality of prediction increased with an increase in resolution and peaked at a resolution of structures at 2.0 A°. There was a noticeable decline in the quality of prediction with the $R^2$ of 0.3 at 3.0 A° resolution.

FIG. 5B shows the relationship between the angular geometries of the structures and the quality of prediction. The angle energy was calculated for all structures in the dataset using the AMBER 96 force-field and was normalized by the number of angles in the structures. For a structure that has been minimized, this quantity would approach zero. However, structures with bad angular geometries have larger values for this term.

The structures were then sorted based on angle energy, and MLR was performed to calculate the goodness of fit. The X-axis of FIG. 4B was divided into bins for angle energies. For example, structures that fell into the 20% bin were the best 20% of the dataset in terms of angular geometries, and the ones that fell into the 40% were the best 40%, which included the structures in the top 20%. FIGS. 5C and 5D are similar plots with the bond energy and bond energy plus angle energy terms. These plots clearly demonstrate the dependence of the quality of prediction on the starting geometry of the structures. This is especially true for FIG. 4C, where $R^2$ dropped from 0.78 for the top 20% of the structures to 0.28 for all the structures. Protein families where the ligand is covalently bonded or had formed a coordination complex with the protein (e.g., human carbonic anhydrase) were not included in the analysis.

Force-field minimizations then were carried out on the ligands in the complexes. The atomtypes of the protein were from the AMBER 96 force-field, and the ligand atoms were assigned the generalized amber force-field (GAFF) atomtypes. The ligand structures were minimized and cleaned up in the active site of the protein using the AMBER 6.0 program. As shown in Table I, there were drastic changes in the heats of formation and solvation free energies for the minimized complexes. The interaction energies of the minimized complexes fell well within the standard normal distribution of the dataset. As a control, similar calculations were done on members of the dataset which were not outliers, and it was found that minimization does not alter the interaction energies drastically. These observations emphasize the importance of the quality of the starting geometries in development of physically based scoring functions.

The role of geometries in the development of structure-based scoring functions has been described above. It is clear that predictive ability is hampered by the presence of structural outliers. Thus, one of the objectives of the present invention was to obtain the best predictive model from a dataset having considerable noise. Hence, the square of the error in prediction was selected as a measure of quality and the dataset was searched for the complexes for which the error in prediction of free energy was minimal. MLR models were then created for the best 100 and best 90 complexes from the dataset. FIG. 6A shows the scatter plot for the best 100 complexes. The $R^2$ for this set was 0.64 and Spress was 1.88 kcals/mol. As shown in FIG. 6B, the $R^2$ for the best 90 structures was 0.68 with a Spress of 1.4 kcals/mol. The regression equations for the two generalized models for 6 parameter fits were:

Best 100:

$\Delta Gpred = 0.005(\Delta HF) + 0.045(\Delta LJ6) + 0.008(\Delta Gsolv) + 0.003(\Delta polarSA) + 0.0003(\Delta apolarSA) + 0.011 (rotatable\_bonds) - 5.36$ Best 90:

$\Delta Gpred = 0.005(\Delta HF) + 0.04(\Delta LJ6) + 0.008(\Delta Gsolv) + 0.002(\Delta polarSA) + 0.001(\Delta apolarSA) + 0.012 (rotatable\_bonds) - 5.574$ The predictive capability of the generalized model derived from the best 100 structures was tested on different families of protein-ligand complexes. Experimental free energies versus the absolute QMScore were also plotted. FIGS. 7A and 7B show the scatter plots for predicted binding free energy versus experimental binding free energies for 25 HIV-1 proteases. The $R^2$ for predicted free energy was 0.51 and for the QMScore, the $R^2$ was 0.25.

The $R^2$ for the QMScore without the single outlier was 0.4. The RMSE of prediction was 1.15 kcals/mol. FIG. 7C shows the predicted free energy and QMScore for sixteen serine proteases. The RMSE of prediction was 10 kcals/mol. Despite having a good $R^2$, the RMSE for serine proteases was very large. This probably was due to the fact that, although the trend was captured by the generalized model, the scale was not. The experimental free energy scale for this family ranged from −2 to −12 kcals/mol, whereas the predicted free energy ranged from −7 to −11 kcals/mol. The $R^2$ for the predicted free energy was 0.72. As shown in FIG. 7D, the $R^2$ for the QMScore was 0.77. FIGS. 7E and 7F show the predicted free energy and the QMScore for fourteen human carbonic anhydrase complexes. The $R^2$ for both the predicted free energy and the QMScore were high, 0.81 and 0.84 respectively. However, the RMSE for prediction was 14.6 kcals/mol.

These results indicate an inherent problem in generalized regression models. A large value for the intercept and very small values for the coefficients for the different terms lead to a prediction in the vicinity of the mean of the distribution for dependent variable, in this case the experimental free energy of binding. However, the corresponding QMScore for all of these families has a similar $R^2$ of prediction, which demonstrates that the method of the present invention was capable of capturing important features of binding.

All of the calculated terms were fit to experimental free energy of binding for the complexes in the dataset using the ordinary least squares (OLS) method and multiple linear regression. The dependent variable or the experimental free energy of binding ($\Delta G_{exp}$) was fit to six independent variables viz., $\Delta HF$ (Heat of formation), $\Delta LJ6$ ($R^6$ part of Lennard-Jones interaction), $\Delta G_{solv}$ (solvation), $\Delta SA_{polar}$ (Polar Surface Area), $\Delta SA_{apolar}$ (Apolar Surface Area), and number of freely rotatable bonds. The resultant master equation is:

$\Delta Gpred = \alpha(\Delta HF) + \beta(\Delta LJ6) + \gamma(\Delta Gsolv) + \delta(\Delta polarSA) + \in(\Delta apolarSA) + \phi(rotatable\_bonds)$ The coefficients estimated by the master equation were used to calculate the predicted binding free energy ($\Delta G_{pred}$) and square of the correlation coefficient ($R^2$). Another measure of success of prediction, $S_{press}$ was calculated as:

$$S_{press} = \sqrt{\frac{\sum (Ypred - Yobs)^2}{(N - k - 1)}}$$

where Ypred is the predicted or calculated free energy of binding, Yobs is the observed or experimental value, N is size of the dataset, and k is the number of independent variables used in the regression model.

CONCLUSIONS

The results show the dependence of predictive capability on geometry of the protein-ligand complex and the effect of geometry optimization on structural outliers. These results point towards the importance of good starting geometries on physically based scoring functions and to obtain accurate protonation states specifically for the imidazole rings and atoms involved in the hydrogen bond-type interactions.

Because the x-ray crystallographic data lack hydrogens, accurate modeling becomes critical—even more so when highly sensitive QM Hamiltonians are used. The protonation state of the protein-ligand complex at crystallographic conditions may differ from the protonation state in the binding assay conditions. Hence, the quality of the experimental data also plays an important role.

Table II shows the differences between Ki's measured in crystallographic conditions and binding assay conditions. For the HIV protease set there is a difference of approximately 1.5 pH units between crystallographic and assay conditions. This can lead to changes in protonation of the active site atoms. The different conditions also reflect the differences in measured Ki's. There is approximately 1.2 kcals/mol difference in binding free energy for the different conditions from the examples in Table II. Binding data in the literature also comes in different forms including binding free energies calculated using isothermal titration calorimetry (ITC), Ki's, Kd's and IC50s. Table II also highlights the difference between these descriptors. The most striking example is that of Endothiapepsin with ligand PD125754. The difference in binding free energy between the Ki and IC50 for the same ligand is approximately 4 kcals/mol. Factoring an average of 1.5 kcals/mol margin of error in the experimental quantities would result in an improvement of the present inventors' predicted values, which have a RMSE of ~2.5 kcals/mol.

Another important issue is the presence of water molecules in the active site. In most cases, during ligand binding, water in the active site is replaced by the incoming ligand. However, in some cases, resident water molecules make key hydrogen bond interactions between the protein and the ligand. Examples of such complexes include Endothiapepsin with PD125754 and PD125967, and complexes in the aspartic proteinase family.

While the invention has been particularly shown and described with reference to preferred embodiments thereof, it will be understood by those skilled in the art that various alterations in form and detail may be made therein without departing from the spirit and scope of the invention.

The invention claimed is:

1. A computational method for designing a drug by predicting free energy of binding ($\Delta G_{bind}$) of a protein-receptor ligand complex using a computer, wherein the free energy of binding is decomposed into a gas-phase interaction energy ($\Delta G_b^g$) and free energy of solvation ($G_{sol}$), the gas-phase interaction energy ($\Delta G_b^g$) is the difference in the heat of formation ($\Delta HF$) of said protein-receptor ligand complex and is calculated as the sum of enthalpic free energy ($\Delta H_b^g$) and entropic free energy ($\Delta S_b^g$), the entropic free energy ($\Delta S_b^g$) is comprised of a conformational entropy component and a solvent entropy component; and the enthalpic energy ($\Delta H_b^g$) is the sum of electrostatic free energy and nonpolar free energy, said nonpolar free energy having a dispersive portion and an attractive portion, wherein said dispersive portion is calculated from a Lennard-Jones potential using an AMBER 96 force-field algorithm for non-bonded atoms, comprising:

preprocessing said protein-receptor ligand complex by protonating heavy atoms of the protein and the ligand;

calculating the electrostatic free energy of said protein-receptor ligand complex using a quantum mechanical Hamiltonian and/or a quantum mechanical/molecular mechanical approach using a computer;

estimating the conformational entropy component of said protein-receptor ligand complex by calculating its vibrational entropy;

calculating the solvent entropy component of said protein-receptor ligand complex by estimating the changes in the polar ($\Delta polarSA$) and apolar ($\Delta apolorSA$) exposed surface area of the protein, wherein the estimation of the exposed surface area of the protein comprises using a probe radius of about 1.4 A°;

calculating the free energy of solvation ($G_{sol}$) of the protein ($\Delta G_{solv}^{protein}$), the ligand ($\Delta G_{solv}^{ligand}$) and said protein-receptor ligand complex ($\Delta G_{solv}^{protein-ligand}$) by using a Poisson-Boltzmann-based self-consistent reaction field algorithm implemented in the computer program DIVCON, wherein the free energy of solvation ($G_{sol}$) is calculated by a computer as the sum of the reaction field (electrostatic $G_{RF}$), a solute wave function distortion (Gwfd) and a hydrophobic (Gnp) term, and wherein the Poisson-Boltzmann-based self-consistent reaction field algorithm is performed in a computer for each self-consistent function cycle until the solute wave function is self-consistent with the solvent reaction field;

calculating the free energy of binding ($\Delta G_{bind}$) in a computer by the following formula:

$$\Delta G_{bind} = \Delta G_b^g + (\Delta G_{solv}^{protein-ligand} - \Delta G_{solv}^{protein} - \Delta G_{solv}^{ligand}),$$

wherein the free energy of binding ($\Delta G_{bind}$) is also a linear combination of the following terms, as follows:

$$\Delta Gpred = f(\Delta H, \Delta Gsolv, T\Delta S)$$

$$\Delta H = \alpha(\Delta HF) + \beta(\Delta LJ6)$$

$$\Delta Gsolv = \gamma(\Delta Gsolv)$$

$$T\Delta S = \delta(\Delta polarSA) + \in(\Delta apolarSA) + \phi(\text{rotatable\_bonds})$$

where $\Delta G_{pred}$ is the predicted free energy of binding, $\Delta H$ is the enthalpy, $\Delta HF$ is the heat of formation portion of the interaction energy, $\Delta LJ6$ is the attractive portion of the nonpolar interaction energy and $\Delta G_{solv}$ is the free energy of solvation;

calculating an absolute binding free energy score (QMScore) and comparing the QMScore to an experimental free energy value, wherein the QMScore is the sum of all of the following terms:

$$\Delta Gpred = f(\Delta H, \Delta Gsolv, T\Delta S)$$

$$\Delta H = \alpha(\Delta HF) + \beta(\Delta LJ6)$$

$$\Delta Gsolv = \gamma(\Delta Gsolv)$$

$$T\Delta S = \delta(\Delta polarSA) + \in(\Delta apolarSA)$$

and using multiple linear regression to determine coefficients or weights to construct a linear interaction energy model, wherein said linear interaction energy model then is used to compute the free energy of binding of said protein receptor-ligand complex, wherein a predictive capability calculated as above is rendered as a plot further output to a user, showing complexes of the dataset, of the experimental binding free energy ($\Delta G_{exp}$), calculated as $-RT \ln K_i$ versus the calculated total score, and which plot demonstrates the predicted drug design;

selecting the drug candidate according to said plot.

2. The method of claim 1, wherein the quantum mechanical Hamiltonian is selected from the group consisting of semiempirical, Hartree-Fock (ab initio), density functional theory and quantum Monte Carlo.

3. The method of claim 1, further comprising calculating the electrostatic free energy of the protein-ligand complex by using a quantum mechanical semiempirical density matrix divide and conquer (D&C) algorithm implemented by a computer program named DIVCON at the AM1 level of theory, wherein DIVCON calculates the gas phase heat of formation of a molecule, said gas phase heat of formation comprised of electronic energy and a core-core repulsion.

4. The method of claim 3, wherein the semiempirical Hamiltonian is a linear scaling density matrix divide and conquer (D&C) algorithm that is capable of solving a Schrodinger equation for a large molecule, by dividing the molecule into subsystems and replacing a Fock matrix diagonalization for the molecule into a series of subsystem diagonalizations, and wherein for each subsystem ($\alpha$), a localized Roothan-Hall equation is solved.

5. The method of claim 4, wherein the density matrix divide and conquer (D&C) algorithm is implemented in parallel using a replicated data strategy, said parallel implementation comprising:
    breaking up the work across the number of processors above diagonalization so as to avoid parallel diagonalization; and
    load balancing subsystems across processors employing a Greedy algorithm that uses the number of orbitals in a subsystem and completion time per subsystem to balance the work load efficiently across processors.

6. The method of claim 1, wherein the ligand is a drug candidate selected from the group consisting of an inhibitor, an agonist and other low molecular weight molecules.

7. A computational method for designing a drug by predicting free energy of binding ($\Delta G_{bind}$) of a protein-receptor ligand complex using a computer, wherein the free energy of binding is decomposed into a gas-phase interaction energy ($\Delta G_b^g$) and free energy of solvation ($G_{sol}$), the gas-phase interaction energy ($\Delta G_b^g$) is the difference in the heat of formation ($\Delta HF$) of said protein-receptor ligand complex and is calculated as the sum of enthalpic free energy ($\Delta H_b^g$) and entropic free energy ($\Delta G_b^g$), the entropic free energy ($\Delta S_b^g$) is comprised of a conformational entropy component and a solvent entropy component; and the enthalpic energy ($\Delta H_b^g$) is the sum of electrostatic free energy and nonpolar free energy, said nonpolar free energy having a dispersive portion and an attractive portion, wherein said dispersive portion is calculated from a Lennard-Jones potential using an AMBER 96 force-field algorithm for non-bonded atoms, comprising:
    preprocessing said protein-receptor ligand complex by protonating heavy atoms of the protein and the ligand;
    calculating the electrostatic free energy of said protein-receptor ligand complex using a quantum mechanical Hamiltonian and/or a quantum mechanical/molecular mechanical approach using a computer;
    estimating the conformational entropy component of said protein-receptor ligand complex by calculating its vibrational entropy;
    calculating the solvent entropy component of said protein-receptor ligand complex by estimating the changes in the polar ($\Delta$polarSA) and apolar ($\Delta$apolorSA) exposed surface area of the protein, wherein the estimation of the exposed surface area of the protein comprises using a probe radius of about 1.4 A°;
    calculating the free energy of solvation ($G_{sol}$) of the protein ($\Delta G_{solv}^{protein}$), the ligand ($\Delta G_{solv}^{ligand}$) and said protein-receptor ligand complex ($\Delta G_{solv}^{protein-ligand}$) by using a Poisson-Boltzmann-based self-consistent reaction field algorithm implemented in the computer program DIVCON, wherein the free energy of solvation ($G_{sol}$) is calculated by a computer as the sum of the reaction field (electrostatic $G_{RF}$), a solute wave function distortion (Gwfd) and a hydrophobic (Gnp) term, and wherein the Poisson-Boltzmann-based self-consistent reaction field algorithm is performed in a computer for each self-consistent function cycle until the solute wave function is self-consistent with the solvent reaction field;
    calculating the free energy of binding ($\Delta G_{bind}$) in a computer by the following formula:

$$\Delta G_{bind} = \Delta G_b^g + (\Delta G_{solv}^{protein-ligand} - \Delta G_{solv}^{protein} - \Delta G_{solv}^{ligand}),$$

wherein the free energy of binding ($\Delta G_{bind}$) is also a linear combination of the following terms, as follows:

$$\Delta Gpred = f(\Delta H, \Delta Gsolv, T\Delta S)$$

$$\Delta H = \alpha(\Delta HF) + \beta(\Delta LJ6)$$

$$\Delta Gsolv = \gamma(\Delta Gsolv)$$

$$T\Delta S = \delta(\Delta polarSA) + \in(\Delta apolarSA) + \phi(\text{rotatable\_bonds})$$

where $\Delta G_{pred}$ is the predicted free energy of binding, $\Delta H$ is the enthalpy, $\Delta HF$ is the heat of formation portion of the interaction energy, $\Delta LJ6$ is the attractive portion of the nonpolar interaction energy and $\Delta G_{solv}$ is the free energy of solvation;
    calculating an absolute binding free energy score (QMScore) and comparing the QMScore to an experimental free energy value, wherein the QMScore is the sum of all of the following terms:

$$\Delta Gpred = f(\Delta H, \Delta Gsolv, T\Delta S)$$

$$\Delta H = \alpha(\Delta HF) + \beta(\Delta LJ6)$$

$$\Delta Gsolv = \gamma(\Delta Gsolv)$$

$$T\Delta S = \delta(\Delta polarSA) + \in(\Delta apolarSA)$$

and using multiple linear regression to determine coefficients or weights to construct a linear interaction energy model, wherein said linear interaction energy model then is used to compute the free energy of binding of said protein receptor-ligand complex, wherein a predictive capability calculated as above is rendered as a plot further output to a user, showing complexes of the dataset, of the experimental binding free energy ($\Delta G_{exp}$), calculated as $-RT \ln K_i$ versus the calculated total score, and which plot demonstrates the predicted drug design;
    selecting the drug candidate according to said plot; and binding at least one molecule of said drug candidate thus selected to an active site in a protein by the drug candidate's either replacing water in said active site of said protein or binding via hydrogen bond interactions with said active site of said protein.

8. A computational method for designing a drug by predicting free energy of binding ($\Delta G_{bind}$) of a protein-receptor ligand complex using a computer, wherein the free energy of binding is decomposed into a gas-phase interaction energy ($\Delta G_b^g$) and free energy of solvation ($G_{sol}$), the gas-phase interaction energy ($\Delta G_b^g$) is the difference in the heat of formation ($\Delta HF$) of said protein-receptor ligand complex and is calculated as the sum of enthalpic free energy ($\Delta_b^g$) and entropic free energy ($\Delta S_b^g$), the entropic free energy ($\Delta S_b^g$) is comprised of a conformational entropy component and a solvent entropy component; and the enthalpic energy ($\Delta H_b^g$) is the sum of electrostatic free energy and nonpolar free energy, said nonpolar free energy having a dispersive portion and an attractive portion, wherein said dispersive portion is calculated from a Lennard-Jones potential using an AMBER 96 force-field algorithm for non-bonded atoms, comprising:
    preprocessing said protein-receptor ligand complex by protonating heavy atoms of the protein and the ligand;

calculating the electrostatic free energy of said protein-receptor ligand complex using a quantum mechanical Hamiltonian and/or a quantum mechanical/molecular mechanical approach using a computer;

estimating the conformational entropy component of said protein-receptor ligand complex by calculating its vibrational entropy;

calculating the solvent entropy component of said protein-receptor ligand complex by estimating the changes in the polar ($\Delta$polarSA) and apolar ($\Delta$apolorSA) exposed surface area of the protein, wherein the estimation of the exposed surface area of the protein comprises using a probe radius of about 1.4 A°;

calculating the free energy of solvation ($G_{sol}$) of the protein ($\Delta G_{solv}^{protein}$), the ligand ($\Delta G_{solv}^{ligand}$) and said protein-receptor ligand complex ($\Delta G_{solv}^{protein-ligand}$) by using a Poisson-Boltzmann-based self-consistent reaction field algorithm implemented in the computer program DIV-CON, wherein the free energy of solvation ($G_{sol}$) is calculated by a computer as the sum of the reaction field (electrostatic $G_{RF}$), a solute wave function distortion (Gwfd) and a hydrophobic (Gnp) term, and wherein the Poisson-Boltzmann-based self-consistent reaction field algorithm is a computer is performed for each self-consistent function cycle until the solute wave function is self-consistent with the solvent reaction field;

calculating the free energy of binding ($\Delta G_{bind}$) in a computer by the following formula:

$$\Delta G_{bind} = \Delta G_b^g + (\Delta G_{solv}^{protein-ligand} - \Delta G_{solv}^{protein} - \Delta G_{solv}^{ligand}),$$

wherein the free energy of binding ($\Delta G_{bind}$) is also a linear combination of the following terms, as follows:

$$\Delta Gpred = f(\Delta H, \Delta Gsolv, T\Delta S)$$

$$\Delta H = \alpha(\Delta HF) + \beta(\Delta LJ6)$$

$$\Delta Gsolv = \gamma(\Delta Gsolv)$$

$$T\Delta S = \delta(\Delta polarSA) + \in(\Delta apolarSA) + \phi(\text{rotatable\_bonds})$$

where $\Delta G_{pred}$ is the predicted free energy of binding, $\Delta H$ is the enthalpy, $\Delta HF$ is the heat of formation portion of the interaction energy, $\Delta LJ6$ is the attractive portion of the non-polar interaction energy and $\Delta G_{solv}$ is the free energy of solvation;

calculating an absolute binding free energy score (QMScore) and comparing the QMScore to an experimental free energy value, wherein the QMScore is the sum of all of the following terms:

$$\Delta Gpred = f(\Delta H, \Delta Gsolv, T\Delta S)$$

$$\Delta H = \alpha(\Delta HF) + \beta(\Delta LJ6)$$

$$\Delta Gsolv = \gamma(\Delta Gsolv)$$

$$T\Delta S = \delta(\Delta polarSA) + \in(\Delta apolarSA)$$

and using multiple linear regression to determine coefficients or weights to construct a linear interaction energy model, wherein said linear interaction energy model then is used to compute the free energy of binding of said protein receptor-ligand complex, wherein a predictive capability calculated as above is rendered as a plot further output to a user, showing complexes of the dataset, of the experimental binding free energy ($\Delta G_{exp}$), calculated as $-RT \ln K_i$ versus the calculated total score, and which plot demonstrates the predicted drug design;

selecting the drug candidate according to said plot; and binding at least one molecule of said drug candidate thus selected to a receptor site by the drug candidate's either replacing water in said receptor site or binding via hydrogen bond interactions with said receptor site.

\* \* \* \* \*